US012674059B2

(12) United States Patent
Bartholomew et al.

(10) Patent No.: US 12,674,059 B2
(45) Date of Patent: Jul. 7, 2026

(54) VIOLET EXCITABLE TANDEM DYES, AND METHODS FOR MAKING AND USING THE SAME

(71) Applicant: Becton, Dickinson and Company, Franklin Lakes, NJ (US)

(72) Inventors: Glenn Bartholomew, Escondido, CA (US); David Michel Moureau, San Diego, CA (US); Itzel Vaca, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 720 days.

(21) Appl. No.: 18/120,554

(22) Filed: Mar. 13, 2023

(65) Prior Publication Data

US 2023/0295440 A1 Sep. 21, 2023

Related U.S. Application Data

(60) Provisional application No. 63/322,120, filed on Mar. 21, 2022.

(51) Int. Cl.
*C09B 69/00* (2006.01)
*C09B 69/10* (2006.01)
(Continued)

(52) U.S. Cl.
CPC ..... *C09B 69/109* (2013.01); *G01N 33/54326* (2013.01); *G01N 33/563* (2013.01);
(Continued)

(58) Field of Classification Search
CPC .................. C09B 69/109; C09B 69/10; G01N 33/54326; G01N 33/563; G01N 33/582;
(Continued)

(56) References Cited

U.S. PATENT DOCUMENTS 3,989,381 A 11/1976 Fulwylet
D339,194 S 9/1993 Telang
(Continued)

FOREIGN PATENT DOCUMENTS

CN 113383043 9/2021
EP 0672458 A2 9/1995
(Continued)

OTHER PUBLICATIONS

Bioconjuagate Chem. 2016, vol. 27, No. 5, pp. 1525-1531.*
(Continued)

*Primary Examiner* — Eisa B Elhilo
(74) *Attorney, Agent, or Firm* — Travis Young; Bret E. Field; Bozicevic, Field & Francis LLP

(57) ABSTRACT

Violet excitable tandem dyes are provided. Tandem dyes of embodiments of the invention include: a non-conjugated polymeric backbone; one or more violet excitable donor fluorophores linked to the non-conjugated polymeric backbone; and one or more acceptor fluorophores linked to the non-conjugated polymeric backbone; where the donor and acceptor fluorophores are in energy transfer relationship. Also provided are methods of making and using the tandem dyes, as well as kits that include the dyes and find use in embodiments of the methods.

19 Claims, 3 Drawing Sheets

(51) Int. Cl.

| | |
|---|---|
| ***G01N 33/543*** | (2006.01) |
| ***G01N 33/563*** | (2006.01) |
| ***G01N 33/58*** | (2006.01) |
| ***G01N 33/68*** | (2006.01) |

(52) U.S. Cl.

CPC ........... *G01N 33/582* (2013.01); *G01N 33/68* (2013.01); *G01N 2446/90* (2013.01)

(58) Field of Classification Search

CPC ... G01N 33/68; G01N 2446/90; G01N 33/533

USPC .............................................................. 8/647

See application file for complete search history.

(56) References Cited

U.S. PATENT DOCUMENTS

| | | | |
|---|---|---|---|
| 5,574,232 | A | 11/1996 | Davidson et al. |
| 5,641,457 | A | 6/1997 | Vardanega et al. |
| 6,079,836 | A | 6/2000 | Burr et al. |
| 6,372,506 | B1 | 4/2002 | Norton |
| 6,881,580 | B2 | 4/2005 | Hall et al. |
| 7,153,475 | B2 | 12/2006 | Hill et al. |
| D676,567 | S | 2/2013 | Van Den Engh |
| 8,455,258 | B2 | 6/2013 | Quake et al. |
| 8,727,132 | B2 | 5/2014 | Miltenyi et al. |
| 8,795,500 | B2 | 8/2014 | Shinoda |
| D715,925 | S | 10/2014 | Suzuki |
| D717,438 | S | 11/2014 | Lin |
| 9,592,483 | B2 | 3/2017 | Fox et al. |
| D802,150 | S | 11/2017 | Lund |
| 10,221,844 | B2 | 3/2019 | Lofstrom et al. |
| 10,508,990 | B2 | 12/2019 | Fox et al. |
| 10,914,671 | B2 | 2/2021 | Norton et al. |
| 2004/0025602 | A1 | 2/2004 | Norton |
| 2004/0062685 | A1 | 4/2004 | Norton |
| 2004/0142463 | A1 | 7/2004 | Walker et al. |
| 2005/0011582 | A1 | 1/2005 | Haug |
| 2006/0118167 | A1 | 6/2006 | Neas et al. |
| 2011/0020855 | A1 | 1/2011 | Shinoda et al. |
| 2011/0024615 | A1 | 2/2011 | Tanner et al. |
| 2011/0137018 | A1 | 6/2011 | Chabg-Yen et al. |
| 2011/0217723 | A1 | 9/2011 | Durack |
| 2011/0259749 | A1 | 10/2011 | Kanda |
| 2011/0271746 | A1 | 11/2011 | Shinoda |
| 2011/0284378 | A1 | 11/2011 | Shinoda |
| 2012/0164718 | A1 | 6/2012 | Bishop et al. |
| 2012/0202237 | A1 | 8/2012 | Sedoglavich et al. |
| 2012/0276621 | A1 | 11/2012 | Van Den Engh |
| 2013/0330739 | A1 | 12/2013 | Yu |
| 2014/0078502 | A1 | 3/2014 | Buchanan et al. |
| 2014/0120570 | A1 | 5/2014 | Yu et al. |
| 2014/0170697 | A1 | 6/2014 | Sharpe et al. |
| 2015/0050638 | A1 | 2/2015 | Marquette |
| 2015/0330385 | A1 | 11/2015 | Lofstrom et al. |
| 2016/0041082 | A1 | 2/2016 | Van Den Engh |
| 2016/0266131 | A1* | 9/2016 | Liang ..................... C08G 61/02 |
| 2017/0299493 | A1 | 10/2017 | Norton |
| 2020/0190253 | A1 | 6/2020 | Easwaran et al. |
| 2020/0392346 | A1* | 12/2020 | Bartholomew ......... C09B 69/00 |
| 2021/0253864 | A1* | 8/2021 | Matray .................. C07F 9/098 |
| 2023/0314418 | A1* | 10/2023 | Moureau .............. G01N 33/533 436/547 |

FOREIGN PATENT DOCUMENTS

| | | | |
|---|---|---|---|
| JP | 4-500008 | A | 1/1992 |
| JP | 2000-516345 | A | 12/2000 |
| JP | 2015512955 | A | 4/2015 |
| WO | WO 90/04019 | A1 | 4/1990 |
| WO | WO 99/26067 | A1 | 5/1999 |
| WO | WO 2010/033140 | A2 | 3/2010 |
| WO | WO 2013119924 | A1 | 8/2013 |

OTHER PUBLICATIONS

Xia, et al. "Influence of Nanostructure on the Exciton Dynamics of Multichromophore Donor-Acceptor Block Copolymers", ACS Nano May 23, 2017; 11(5):4593-4598.

Jayasinghe et al. "Sterile and Disposable Fluidic Subsystem Suitable for Clinical High Speed Fluorescence-Activated Cell Sorting", Cytometry Part B (Clinical Cytometry) 708:344-354 (2006).

Miltenyi Biotec GMBH, CliniMACS® Cell Separation Systems, Product Catalog 2008, 48 pages.

Miltenyi Biotec GMBH, CliniMACS® User Manual, US Edition, Software 2.40, Jan. 2014, 128 pages.

Miltenyi Biotec GMBH, CliniMACS® User Manual for the CliniMACS® CD34 Reagent System, Jan. 2014, 102 pages.

Sandin et al. "Magnetophoresis and cytometry with magnetic microparticles", International Congress Series, Jun. 2007, vol. 1300, pp. 271-274.

Yang et al. "Micro flow cytometry utilizing a magnetic bead-based immunoassay for rapid virus detection", Biosensors and Bioelectronics, Dec. 1, 2008, vol. 24, No. 4, pp. 855-862.

Naganbabu, et al., "Multiexcitation Fluorogenic Labeling of Surface, Intracellular, and Total Protein Pools in Living Cells", Bioconjugate Chem., 2016, vol. 27, No. 5, pp. 1525-1531.

Kesavan, et al, "Carbazole substituted boron dipyrromethenes", Dalton Transaction, vol. 43, No. 32, 2014, pp. 12405-12413.

* cited by examiner

VIOLET EXCITABLE TANDEM DYES, AND METHODS FOR MAKING AND USING THE SAME

CROSS-REFERENCE TO RELATED APPLICATION

Pursuant to 35 U.S.C. § 119 (e), this application claims priority to the filing dates of U.S. Provisional Patent Application Ser. No. 63/322,120 filed Mar. 21, 2022, the disclosure of which application is incorporated herein by reference in their entirety.

INTRODUCTION

Fluorescent dyes are compounds which, when irradiated with light of a wavelength which they absorb, emit light of a (usually) different wavelength. Fluorescent dyes find use in a variety of applications in biochemistry, biology and medicine, e.g., in diagnostic kits, in microscopy or in drug screening. Fluorescent dyes are characterized by a number of parameters allowing a user to select a suitable dye depending on the desired purpose. Parameters of interest include the excitation wavelength maximum, the emission wavelength maximum, the Stokes shift, the extinction coefficient, the fluorescence quantum yield and the fluorescence lifetime. Dyes may be selected according to the application of interest in order to, e.g., allow penetration of exciting radiation into biological samples, to minimize background fluorescence and/or to achieve a high signal-to-noise ratio.

Molecular recognition involves the specific binding of two molecules. Molecules which have binding specificity for a target biomolecule find use in a variety of research and diagnostic applications, such as the labelling and separation of analytes, flow cytometry, in situ hybridization, enzyme-linked immunosorbent assays (ELISAs), western blot analysis, magnetic cell separations and chromatography. Target biomolecules may be detected by labelling with a fluorescent dye.

Some applications, such as flow cytometry applications, employ combinations or panels of differentially fluorescently labeled specific binding members, such as antibodies, for the detection of multiple different targets, e.g., internal or cell surface markers. In such applications, multiple different fluorescent dyes are employed with the same sample, where the multiple different fluorescent dyes are distinguishable from each other in terms of excitation and/or emission maxima. One type of fluorescent dye that finds use in such applications is a tandem fluorescent dye. Tandem fluorescent dyes are compounds having two covalently linked different fluorophores, which fluorophores may be covalently Inked to each other directly or through a linking group. One of the fluorophores serves as donor fluorophore and the other fluorophore acts as acceptor fluorophore. The donor and acceptor fluorophores together form a fluorescence-resonance energy transfer (FRET) pair. Such FRET pairs behave as a unique dye that has the excitation properties of the donor fluorophore and the emission properties of the acceptor fluorophore.

SUMMARY

The inventors have realized that there is a need for tandem fluorescent dyes where the donor fluorophore is excited in the violet wavelength range, e.g., so as to be excitable by commonly available violet lasers. Embodiments of the invention satisfy this need.

Violet excitable tandem dyes are provided. Tandem dyes of embodiments of the invention include: a non-conjugated polymeric backbone; one or more violet excitable donor fluorophores linked to the non-conjugated polymeric backbone; and one or more acceptor fluorophores linked to the non-conjugated polymeric backbone; where the donor and acceptor fluorophores are in energy transfer relationship. Also provided are methods of making and using the tandem dyes, as well as kits that include the dyes and find use in embodiments of the methods.

BRIEF DESCRIPTION OF THE DRAWINGS

The invention may be best understood from the following detailed description when read in conjunction with the accompanying drawings. Included in the drawings are the following figures.

DEFINITIONS

Figure 1:
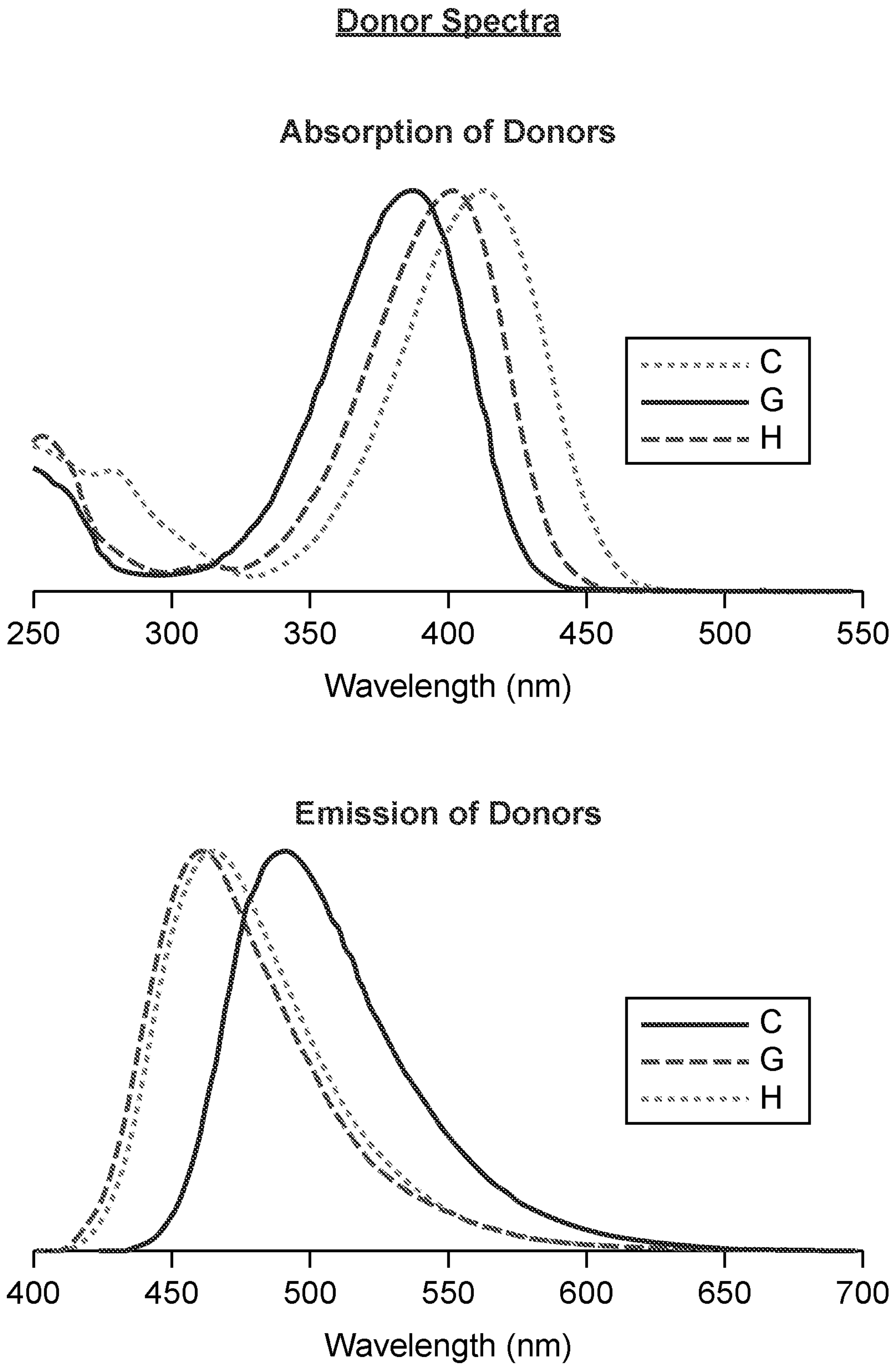
FIG. 1 provides donor absorption and emission spectra for three coumarin violet excitable donor fluorophores that may be employed in tandem dyes of embodiments of the invention.

As used herein, the terms “chemoselective functional group” and “chemoselective tag” are used interchangeably and refer to a functional group that can selectively react with another compatible functional group to form a covalent bond, in some cases, after optional activation of one of the functional groups. Chemoselective functional groups of interest include, but are not limited to, thiols and maleimide or iodoacetamide, amines and carboxylic acids or active esters thereof, as well as groups that can react with one another via Click chemistry, e.g., azide and alkyne groups (e.g., cyclooctyne groups), tetrazine, transcyclooctene, dienes and dienophiles, and azide, sulfur(VI) fluoride exchange chemistry (SuFEX), sulfonyl fluoride, as well as hydroxyl, hydrazido, hydrazino, aldehyde, ketone, azido, alkyne, phosphine, epoxide, and the like.

As used herein, the term “sample” relates to a material or mixture of materials, in some cases in liquid form, containing one or more analytes of interest. In some embodiments, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term “sample” may also refer to a “biological sample”. As used herein, the term “a biological sample” refers to a whole organism or a subset of its tissues, cells or component parts (e.g., body fluids, including, but not limited to, blood, mucus, lymphatic fluid, synovial fluid, cerebrospinal fluid, saliva, amniotic fluid, amniotic cord blood, urine, vaginal fluid and semen). A “biological sample” can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term “cells” is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The terms "support bound" and "linked to a support" are used interchangeably and refer to a moiety (e.g., a specific binding member) that is linked covalently or non-covalently to a support of interest. Covalent linking may involve the chemical reaction of two compatible functional groups (e.g., two chemoselective functional groups, an electrophile and a nucleophile, etc.) to form a covalent bond between the two moieties of interest (e.g., a support and a specific binding member). In some cases, non-covalent linking may involve specific binding between two moieties of interest (e.g., two affinity moieties such as a hapten and an antibody or a biotin moiety and a streptavidin, etc.). In certain cases, non-covalent linking may involve absorption to a substrate.

The term "polypeptide" refers to a polymeric form of amino acids of any length, including peptides that range from 2-50 amino acids in length and polypeptides that are greater than 50 amino acids in length. The terms "polypeptide" and "protein" are used interchangeably herein. The term "polypeptide" includes polymers of coded and non-coded amino acids, chemically or biochemically modified or derivatized amino acids, and polypeptides having modified peptide backbones in which the conventional backbone has been replaced with non-naturally occurring or synthetic backbones. A polypeptide may be of any convenient length, e.g., 2 or more amino acids, such as 4 or more amino acids, 10 or more amino acids, 20 or more amino acids, 50 or more amino acids, 100 or more amino acids, 300 or more amino acids, such as up to 500 or 1000 or more amino acids. "Peptides" may be 2 or more amino acids, such as 4 or more amino acids, 10 or more amino acids, 20 or more amino acids, such as up to 50 amino acids. In some embodiments, peptides are between 5 and 30 amino acids in length.

As used herein the term "isolated," refers to an moiety of interest that is at least 60% free, at least 75% free, at least 90% free, at least 95% free, at least 98% free, and even at least 99% free from other components with which the moiety is associated with prior to purification.

A "plurality" contains at least 2 members. In certain cases, a plurality may have 5 or more, such as 6 or more, 7 or more, 8 or more, 9 or more, 10 or more, 20 or more, 30 or more, 40 or more, 50 or more, 60 or more, 70 or more, 80 or more, 90 or more, 100 or more, 300 or more, 1000 or more, 3000 or more, 10,000 or more, 100,000 or more members.

Numeric ranges are inclusive of the numbers defining the range.

The term "specific binding" refers to a direct association between two molecules, due to, for example, covalent, electrostatic, hydrophobic, and ionic and/or hydrogen-bond interactions, including interactions such as salt bridges and water bridges. A specific binding member describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus, the members of the pair have the property of binding specifically to each other. Examples of pairs of specific binding members are antigen-antibody, biotin-avidin, hormone-hormone receptor, receptor-ligand, enzyme-substrate. Specific binding members of a binding pair exhibit high affinity and binding specificity for binding with each other. Typically, affinity between the specific binding members of a pair is characterized by a K(dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower KD. In an embodiment, affinity is determined by surface plasmon resonance (SPR), e.g., as used by Biacore systems. The affinity of one molecule for another molecule is determined by measuring the binding kinetics of the interaction, e.g., at 25° C. "Affinity" refers to the strength of binding, increased binding affinity being correlated with a lower KD. In an embodiment, affinity is determined by surface plasmon resonance (SPR), e.g., as used by Biacore systems. The affinity of one molecule for another molecule is determined by measuring the binding kinetics of the interaction, e.g., at 25° C.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a $F(ab')_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

The methods described herein may include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

As used herein, the terms "evaluating", "determining," "measuring," and "assessing," and "assaying" are used interchangeably and include both quantitative and qualitative determinations.

The term "separating", as used herein, refers to physical separation of two elements (e.g., by size or affinity, etc.) as well as degradation of one element, leaving the other intact.

The term "linker" or "linkage" refers to a linking moiety that connects two groups and has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20 or more carbon atoms in length, where the linker may be linear, branched, cyclic or a single atom. In some cases, the linker is a branching linker that refers to a linking moiety that connects three or more groups. In certain cases, one, two, three, four or five or more carbon atoms of a linker backbone may be optionally substituted with a sulfur, nitrogen or oxygen heteroatom. In some cases, the linker backbone includes a linking functional group, such as an ether, thioether, amino, amide, sulfonamide, carbamate, thiocarbamate, urea, thiourea, ester, thioester or imine. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

As used herein, the terms "water solubilizing group", "water soluble group" and WSG are used interchangeably and refer to a group or substituent that is well solvated in aqueous environments e.g., under physiological conditions, and which imparts improved water solubility upon the molecule to which it is attached. A WSG can increase the solubility of a tandem dye or component thereof, e.g., donor or acceptor fluorophore, in a predominantly aqueous solution, as compared to a control tandem dye or component thereof which lacks the WSG. The water solubilizing groups may be any convenient hydrophilic group that is well solvated in aqueous environments.

A variety of water soluble polymer groups can be adapted for use in the WSG of the subject dyes. Any convenient water solubilizing groups (WSG's) may be included in the dyes described herein to provide for increased water-solubility. While the increase in solubility may vary, in some instances the increase (as compared to the compound without the WSG(s)) is 2 fold or more, e.g., 5 fold, 10 fold, 25 fold, 50 fold, 100 fold or more. In some cases, the hydrophilic water solubilizing group is charged, e.g., positively or negatively charged. In certain cases, the hydrophilic water solubilizing group is a neutral hydrophilic group. In some embodiments, the WSG is branched (e.g., as described herein). In certain instances, the WSG is linear. In some embodiments, the WSG is a hydrophilic polymer, e.g., a polyethylene glycol, a modified PEG, a peptide sequence, a peptoid, a carbohydrate, an oxazoline, a polyol, a dendron, a dendritic polyglycerol, a cellulose, a chitosan, or a derivative thereof. Water solubilizing groups of interest include, but are not limited to, carboxylate, phosphonate, phosphate, sulfonate, sulfate, sulfinate, sulfonium, ester, polyethylene glycols (PEG) and modified PEGs, hydroxyl, amine, amino acid, ammonium, guanidinium, pyridinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, $-COOM'$, $-SO_3M'$, $-PO_3M'$, $-NR_3^+$, Y', $(CH_2CH_2O)_pR$ and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, $-(CH_2CH_2O)_{yy}CH_2CH_2XR^{yy}$, $-(CH_2CH_2O)_{yy}CH_2CH_2X-$, $-X(CH_2CH_2O)_{yy}CH_2CH_2-$, glycol, and polyethylene glycol, wherein yy is selected from 1 to 1000, X is selected from O, S, and $NR^{ZZ}$, and $R^{ZZ}$ and $R^{YY}$ are independently selected from H and $C_{1-3}$ alkyl. In some cases, a WSG is $(CH_2)_x(OCH_2CH_2)_yOCH_3$ where each x is independently an integer from 0-20, each y is independently an integer from 0 to 50. In some cases, the water solubilizing group includes a non-ionic polymer (e.g., a PEG polymer) substituted at the terminal with an ionic group (e.g., a sulfonate).

In some embodiments of the formulae, the pendant group of interest includes a substituent selected from $(CH_2)_x(OCH_2CH_2)_yOCH_3$ where each x is independently an integer from 0-20, each y is independently an integer from 0 to 50; and a benzyl optionally substituted with one or more halogen, hydroxyl, $C_1$-$C_{12}$ alkoxy, or $(OCH_2CH_2)_zOCH_3$ where each z is independently an integer from 0 to 50. In some instances, the substituent is $(CH_2)_3(OCH_2CH_2)_{11}OCH_3$. In some embodiments, one or more of the substituents is a benzyl substituted with at least one WSG groups (e.g., one or two WSG groups) selected from $(CH_2)_x(OCH_2CH_2)_yOCH_3$ where each x is independently an integer from 0-20 and each y is independently an integer from 0 to 50.

Multiple WSGs may be included at a single location in the subject dyes via a branching linker. In certain embodiments, the branching linker is an aralkyl substituent, further disubstituted with water solubilizing groups. As such, in some cases, the branching linker group is a substituent of the dye that connects the dye to two or more water solubilizing groups. In certain embodiments, the branching linker is an amino acid, e.g., a lysine amino acid that is connected to three groups via the amino and carboxylic acid groups. In some cases, the incorporation of multiple WSGs via branching linkers imparts a desirable solubility on the dye. In some instances, the WSG is a non-ionic sidechain group capable of imparting solubility in water in excess of 50 mg/mL. In some instances, the WSG is a non-ionic sidechain group capable of imparting solubility in water in excess of 100 mg/mL. In some embodiments, the dye includes substituent(s) selected from the group consisting of, an alkyl, an aralkyl and a heterocyclic group, each group further substituted with a include water solubilizing groups hydrophilic polymer group, such as a polyethylglycol (PEG) (e.g., a PEG group of 6-24 units).

Water soluble polymers of interest that can be utilized in the WSG include polyethylene glycol (PEG) groups or modified PEG groups. Water-soluble polymers of interest include, but are not limited to, polyalkylene oxide based polymers, such as polyethylene glycol "PEG" (See. e.g., "Poly(ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Examples of water soluble polymers of interest include, but are not limited to, those containing a polyalkylene oxide, polyamide alkylene oxide, or derivatives thereof, including polyalkylene oxide and polyamide alkylene oxide comprising an ethylene oxide repeat unit of the formula $—(CH_2—CH_2—O)—$. Further examples of polymers of interest include a polyamide having a molecular weight greater than 1,000 Daltons of the formula $—[C(O)—X—C(O)—NH—Y—NH]n-$ or $—[NH—Y—NH—C(O)—X—C(O)]_n—$, where X and Y are divalent radicals that may be the same or different and may be branched or linear, and n is a discrete integer from 2-100, such as from 2 to 50, and where either or both of X and Y comprises a biocompatible, substantially non-antigenic water-soluble repeat unit that may be linear or branched. Further examples of water-soluble repeat units comprise an ethylene oxide of the formula $—(CH_2—CH_2—O)—$ or $—(O—CH_2—CH_2)—$. The number of such water-soluble repeat units can vary significantly, with the number of such units being from 2 to 500, 2 to 400, 2 to 300, 2 to 200, 2 to 100, 6-100, for example from 2 to 50 or 6 to 50. An example of an embodiment is one in which one or both of X and Y is selected from: $—((CH_2)_{n1}—(CH_2—CH_2—O)_{n2}—(CH_2)—$ or $—((CH_2)_{n1}—(O—CH_2—CH_2)_{n2}—(CH_2)_{n-1}—)$, where n1 is 1 to 6, 1 to 5, 1 to 4, or 1 to 3, and where n2 is 2 to 50, 2 to 25, 2 to 15, 2 to 10, 2 to 8, or 2 to 5. A further example of an embodiment is one in which X is $—(CH_2—CH_2)—$, and where Y is $—(CH_2—(CH_2—CH_2—O)_3—CH_2—CH_2—CH_2)—$ or $—(CH_2—CH_2—CH_2—(O—CH_2—CH_2)_3—CH_2)—$.

The term modified polymer, such as a modified PEG, refers to water soluble polymers that have been modified or derivatized at either or both terminals, e.g., to include a terminal substituent (e.g., a terminal alkyl, substituted alkyl, alkoxy or substituted alkoxy, etc.) and/or a terminal linking functional group (e.g., an amino or carboxylic acid group suitable for attachment via amide bond formation) suitable for attached of the polymer to a molecule of interest (e.g., to a light harvesting chromophore via a branching group). The subject water soluble polymers can be adapted to include any convenient linking groups. It is understood that in some cases, the water soluble polymer can include some dispersity with respect to polymer length, depending on the method of preparation and/or purification of the polymeric starting materials. In some instances, the water soluble polymers are monodisperse.

The water soluble polymer can include one or more spacers or linkers. Examples of spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The water soluble polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of a sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the WSGs disclosed herein.

The water soluble group (WSG) can be capable of imparting solubility in water in excess of 10 mg/mL to the subject dye or polymeric tandem dye, such as in excess of 20 mg/mL, in excess of 30 mg/mL, in excess of 40 mg/mL, in excess of 50 mg/mL, in excess of 60 mg/mL, in excess of 70 mg/mL, in excess of 80 mg/mL, in excess of 90 mg/mL or in excess of 100 mg/mL. In certain cases, the branched non-ionic water soluble group (WSG) is capable of imparting solubility in water (e.g., an aqueous buffer) of 20 mg/mL or more to the subject dye or polymeric tandem dye, such as 30 mg/mL or more, 40 mg/mL or more, 50 mg/mL or more, 60 mg/mL or more, 70 mg/mL or more, 80 mg/mL or more, 90 mg/mL or more, 100 mg/mL or more, or even more. It is understood that water-soluble dipyrromethene-based dye may, under certain conditions, form discrete water solvated nanoparticles in aqueous systems. In certain cases, the water solvated nanoparticles are resistant to aggregation and find use in a variety of biological assays.

The terms "polyethylene oxide", "PEO", "polyethylene glycol" and "PEG" are used interchangeably and refer to a polymeric group including a chain described by the formula $—(CH_2—O—)_n—$ or a derivative thereof. In some embodiments, "n" is 5000 or less, such as 1000 or less, 500 or less, 200 or less, 100 or less, 50 or less, 40 or less, 30 or less, 20 or less, 15 or less, such as 3 to 15, or 10 to 15. It is understood that the PEG polymeric group may be of any convenient length and may include a variety of terminal groups and/or further substituent groups, including but not limited to, alkyl, aryl, hydroxyl, amino, acyl, acyloxy, and amido terminal and/or substituent groups. PEG groups that may be adapted for use in the subject multichromophores include those PEGs described by S. Zalipsky in "Functionalized poly(ethylene glycol) for preparation of biologically relevant conjugates", Bioconjugate Chemistry 1995, 6 (2), 150-165; and by Zhu et al in "Water-Soluble Conjugated Polymers for Imaging, Diagnosis, and Therapy", Chem. Rev., 2012, 112 (8), pp 4687-4735.

The term "alkyl" by itself or as part of another substituent refers to a saturated branched or straight-chain monovalent hydrocarbon radical derived by the removal of one hydrogen atom from a single carbon atom of a parent alkane. Alkyl groups of interest include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group includes from 1 to 20 carbon atoms. In some embodiments, an alkyl group includes from 1 to 10 carbon atoms. In certain embodiments, a lower alkyl group includes from 1 to 6 carbon atoms, such as from 1 to 4 carbon atoms. This term includes, by way of example, linear and branched hydrocarbyl groups such as methyl ($CH_3—$), ethyl ($CH_3CH_2—$), n-propyl ($CH_3CH_2CH_2—$), isopropyl ($(CH_3)_2CH—$), n-butyl ($CH_3CH_2CH_2CH_2—$), isobutyl ($(CH_3)_2CHCH_2—$), sec-butyl ($(CH_3)(CH_3CH_2)CH—$), t-butyl ($(CH_3)_3C—$), n-pentyl ($CH_3CH_2CH_2CH_2CH_2—$), and neopentyl ($(CH_3)_3CCH_2—$).

The term "substituted alkyl" refers to an alkyl group as defined herein wherein one or more carbon atoms in the alkyl chain have been optionally replaced with a heteroatom such as —O—, —N—, —S—, $—S(O)_n—$ (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, $—SO_2$-alkyl, $—SO_2$-aryl, $—SO_2—$ heteroaryl, and $—NR^aR^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkenyl" refers to a monoradical, branched or linear, cyclic or non-cyclic hydrocarbonyl group that comprises a carbon-carbon double bond. Exemplary alkenyl groups include ethenyl, n-propenyl, isopropenyl, n-butenyl, isobutenyl, octenyl, decenyl, tetradecenyl, hexadecenyl, eicosenyl, and tetracosenyl. In some cases the alkenyl group comprises 1 to 24 carbon atoms, such as 1 to 18 carbon atoms or 1 to 12 carbon atoms. The term "lower alkenyl" refers to an alkyl groups with 1 to 6 carbon atoms.

"Alkynyl" or "alkyne" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl ($—C{\equiv}CH$), and propargyl ($—CH_2C{\equiv}CH$).

The term "substituted alkynyl" or "substituted alkyne" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, $—SO_2$-alkyl, $—SO_2$-substituted alkyl, $—SO_2$-aryl, and $—SO_2$-heteroaryl.

"Heterocyclyl" refers to a monoradical, cyclic group that contains a heteroatom (e.g. O, S, N) in as a ring atom and that is not aromatic (i.e. distinguishing heterocyclyl groups from heteroaryl groups). Exemplary heterocyclyl groups include piperidinyl, tetrahydrofuranyl, dihydrofuranyl, and thiocanyl.

"Amino" refers to the group $—NH_2$. The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aryl" by itself or as part of another substituent refers to a monovalent aromatic hydrocarbon radical derived by the removal of one hydrogen atom from a single carbon atom of an aromatic ring system. Aryl groups of interest include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group includes from 6 to 20 carbon atoms. In certain embodiments, an aryl group includes from 6 to 12 carbon atoms. Examples of an aryl group are phenyl and naphthyl.

"Substituted aryl", unless otherwise constrained by the definition for the aryl substituent, refers to an aryl group substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO— alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

"Heteroaryl" by itself or as part of another substituent, refers to a monovalent heteroaromatic radical derived by the removal of one hydrogen atom from a single atom of a heteroaromatic ring system. Heteroaryl groups of interest include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, triazole, benzotriazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$-moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Substituted heteroaryl", unless otherwise constrained by the definition for the substituent, refers to an heteroaryl group substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO— alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl and trihalomethyl.

The term "alkaryl" or "aralkyl" refers to the groups -alkylene-aryl and substituted alkylene-aryl where alkylene, substituted alkylene and aryl are defined herein.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from—O—, —$NR^{10}$—, —$NR^{10}$C(O)—, —C(O)$NR^{10}$— and the like. This term includes, by way of example, methylene (—$CH_2$—), ethylene (—$CH_2CH_2$—), n-propylene (—$CH_2CH_2CH_2$—), iso-propylene (—$CH_2CH(CH_3)$—), (—$C(CH_3)_2CH_2CH_2$—), (—$C(CH_3)_2CH_2C(O)$—), (—$C(CH_3)_2CH_2C(O)NH$—), (—$CH(CH_3)CH_2$—), and the like. "Substituted alkylene" refers to an alkylene group having from 1 to 3 hydrogens replaced with substituents as described for carbons in the definition of "substituted" below.

"Substituted" refers to a group in which one or more hydrogen atoms are independently replaced with the same or different substituent(s). Substituents of interest include, but are not limited to, alkylenedioxy (such as methylenedioxy), -M, —$R^{60}$, —O—, =O, —$OR^{60}$, —$SR^{60}$, —S—, =S, —$NR^{60}R^{61}$, =$NR^{60}$, —$CF_3$, —CN, —OCN, —SCN, —NO, —$NO_2$, =$N_2$, —$N_3$, —$S(O)_2O$—, —$S(O)_2OH$, —$S(O)_2R^{60}$, —$OS(O)_2O$—, —$OS(O)_2R^{60}$, —$P(O)(O^-)_2$, —$P(O)(OR^{60})$ ($O^-$), —$OP(O)(OR^{60})(OR^{61})$, —$C(O)R^{60}$, —$C(S)R^{60}$, —$C(O)OR^{60}$, —$C(O)NR^{60}R^{61}$, —C(O)O—, —C(S) $OR^{60}$, —$NR^{62}C(O)NR^{60}R^{61}$, —$NR^{60}C(S)NR^{60}R^{60}$, —$NR^{60}C(NR^{60})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —S—, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —C(O)O—, —$NR^{60}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^6$, =O, —$OR^{60}$, —$SR^{60}$, —$NR^{60}R^{61}$, —$CF_3$, —CN, —$NO_2$, —$S(O)_2R^{60}$, —$OP(O)(OR)(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group. When the group being substituted is an aryl or heteroaryl group, the substituent(s) (e.g., as described herein) may be referred to as "aryl substituent(s)".

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

"Acyl" refers to a group of formula —C(O)R wherein R is alkyl, alkenyl, or alkynyl. For example, the acetyl group has formula —$C(O)CH_3$.

"Halo" and "halogen" refer to the chloro, bromo, fluoro, and iodo groups.

"Carboxyl", "carboxy", and "carboxylate" refer to the —$CO_2H$ group and salts thereof.

"Sulfonyl" refers to the group —$SO_2R$, wherein R is alkyl, alkenyl, alkynyl, aryl, heteroaryl, heterocyclyl, and substituted versions thereof. Exemplary sulfonyl groups includes —$SO_2CH_3$ and —$SO_2(C_6H_5)$.

Unless otherwise specified, reference to an atom is meant to include all isotopes of that atom. For example, reference to H is meant to include $^1H$, $^2H$ (i.e., D) and $^3H$ (i.e., T), and reference to C is meant to include $^{12}C$ and all isotopes of carbon (such as $^{13}C$). In addition, any groups described include all stereoisomers of that group.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

DETAILED DESCRIPTION

Violet excitable tandem dyes are provided. Tandem dyes of embodiments of the invention include: a non-conjugated polymeric backbone; one or more violet excitable donor fluorophores linked to the non-conjugated polymeric backbone; and one or more acceptor fluorophores linked to the non-conjugated polymeric backbone; where the donor and acceptor fluorophores are in energy transfer relationship. Also provided are methods of making and using the tandem dyes, as well as kits that include the dyes and find use in embodiments of the methods.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Still, certain terms are defined below for the sake of clarity and ease of reference. Further, although any methods and materials similar or equivalent to those described herein can also be used in the practice or testing of the present invention, representative illustrative methods and materials are described herein.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

In further describing various embodiments of the invention, violet excitable tandem dyes are reviewed first in greater detail, followed by a review of methods of using and making the dyes, as well as a review of kits that include the conjugates.

Violect Excitable Tandem Dyes

As summarized above, the present disclosure provides violet excitable fluorescent tandem dye conjugates. Violet excitable tandem dyes are dyes that may be excited by violet light, e.g., violet light provided by a violet laser. In some instances, violet excitable tandem dyes are excitable by light having a wavelength ranging from 350 to 450 nm. The excitation maximum of violet excitable tandem dyes of the invention may vary, and in some embodiments ranges from 375 to 425 nm, such as 390 to 410 nm, e.g., 400 to 410 nm. As such, violet excitable tandem dyes of the invention may be excited by lasers producing light having wavelengths ranging from from 375 to 425 nm, such as 390 to 410 nm, e.g., 400 to 410 nm, where examples of such lasers include, but are no limited to: violet laser diodes (e.g., as described in Telford et al., "Violet laser diodes in flow cytometry: an update," Cytometry A. (Nov. 1, 2006) 69(11):1153-60), and the like.

As summarized above, violet excitable tandem dyes of embodiments of the invention include: a non-conjugated polymeric backbone; one or more violet excitable donor fluorophores linked to the non-conjugated polymeric backbone; and one or more acceptor fluorophores linked to the non-conjugated polymeric backbone, where the donor and acceptor fluorophores are in energy transfer relationship. Each of these components of the violet excitable dyes is now reviewed in greater detail.

Violet Excitable Donor Fluorophores

As summarized above, tandem dyes of the invention include one or more violet excitable donor fluorophores. Violet excitable donor fluorophores are fluorophores that absorb light in the violet wavelength range, e.g., 350 to 450 nm, such as 375 to 425 nm. In certain cases, the violet excitable donor fluorophores have an absorption maxima ranging from 375 to 425 nm, such as 390 to 410 nm, e.g., 400 to 410 nm, e.g., 400 nm, 401 nm, 402 nm, 403 nm, 404 nm, 405 nm, 406 nm, 407 nm, 408 nm, 409 nm and 410 nm. In certain embodiments, the violet excitable donor fluorophores exhibit narrow absorption spectrum. A narrow absorption spectrum is one that has an absorption maxima peak having a full-width half maximum (FWHM) of 35 nm or less, such as 25 nm or less, 20 nm or less, 15 nm or less, 12 nm or less or 10 nm or less, e.g., as measured in ethanol or in phosphate buffered saline (PBS). Donor violet excitable fluorophores of embodiments of the invention may vary. Types of donor violet excitable fluorophores that may be found in tandem dyes of the invention include, but are not limited to: coumarin fluorophores, pyrene fluorophores, triphenyl fluorophores, and the like.

In some instances, the violet excitable donor fluorophore is a coumarin flourophore. Coumarin fluorophores are fluorophores having a coumarin core, which may be described as a benzene molecule with two adjacent hydrogen atoms replaced by a lactone-like chain —=—O—, forming a second six-membered heterocycle that shares two carbons with the benzene ring. The coumarin core may be depicted by the following structure:

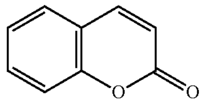 [SMILES: O=c1ccc2ccccc2o1]

Coumarin donore fluorophores of interest include coumarin derivatives. By "coumarin" derivative is meant a molecule comprising a coumarin core, wherein one or more of the coumarin core atoms is substituted or conjugated to a further moiety. In some instances, coumarin fluorophores finding use as violet excitable donor fluorophores in embodiments of the invention are described by the following formula:

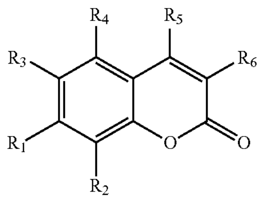

wherein:

$R_1$ is $OR_1'$ or $NR_2'R_3'$, wherein $R_1'$, $R_2'$ and $R_3'$ are independently selected from hydrogen, alkyl, alkenyl, alkynyl, cycloalkyl, cycloalkenyl, cycloalkynyl, aryl, alkaryl, arylalkyl, a water solubilizing group (WSG) or carboxy alkyl, alkyl being optionally substituted by hydroxyl, amino, carboxyl, carboxylic ester, amide, carbamate, or aminoalkyl or a water solubilizing group (WSG); or $R_1'$ and $R_2$ or $R_1'$ and $R_3$ come together to form a 5, 6 or 7-membered ring which is selected from aryl, heterocyclic, heteroaryl, and heteroaromatic; or $R_2$, $R_2$, $R_3'$, and $R_3$ come together independently to form at least one 5, 6 or 7-membered ring which is selected from aryl, heterocyclic, heteroaryl and heteroaromatic;

$R_2$, $R_3$ and $R_4$ are independently selected from hydrogen, halogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, carboxylic ester, amide, carbamate, or aminoalkyl, wherein any of these groups may be further substituted, e.g., with a WSG:

$R_5$ and $R_6$ are independently selected from hydrogen, halogen, alkyl, alkoxy, keto, carboxylate, carboxylic ester, carbamate, amide, amino, alkylamino, benzoimidazolyl, polyether, alkylthio, cyano, nitro, sulfonyl, pyrimidine, purine, wherein any of these groups may be further substituted, e.g., with a WSG.

In some instances, a coumarin donor fluorophore of a tandem dye of the invention is a coumarin donor fluorophore having one of the following formulae:

A

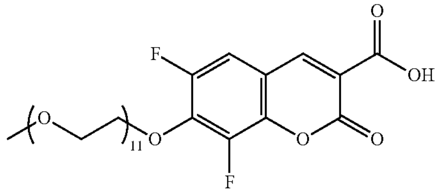

-continued

B

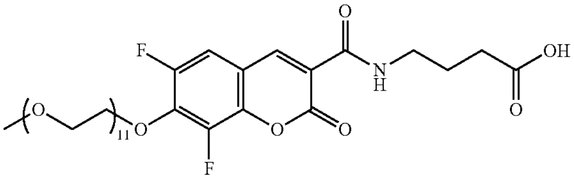

C

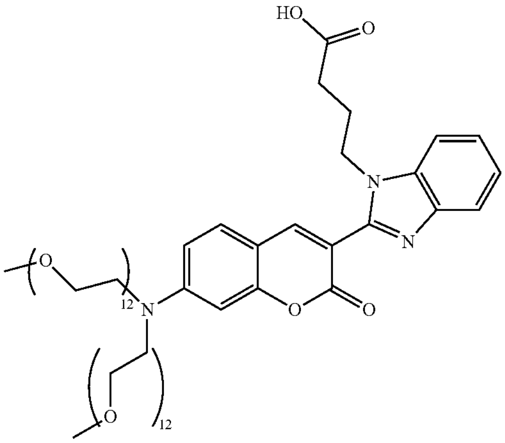

D

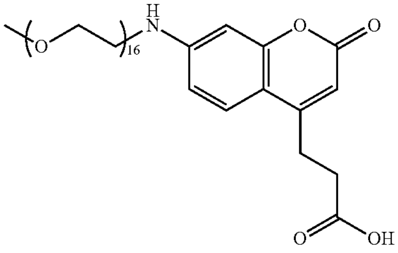

E

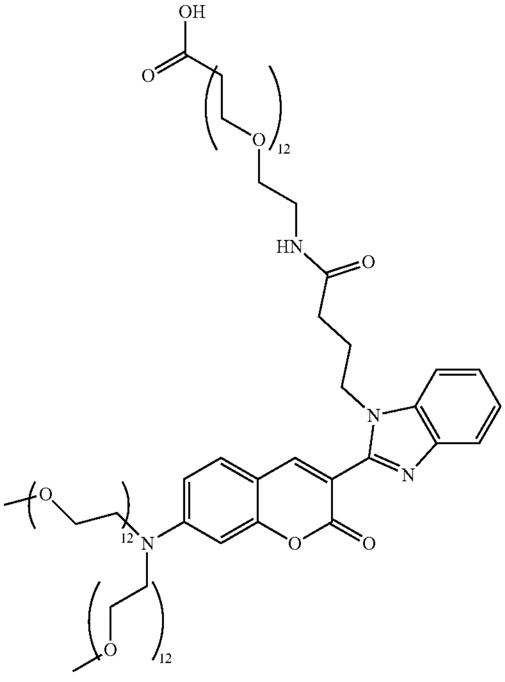

-continued

F

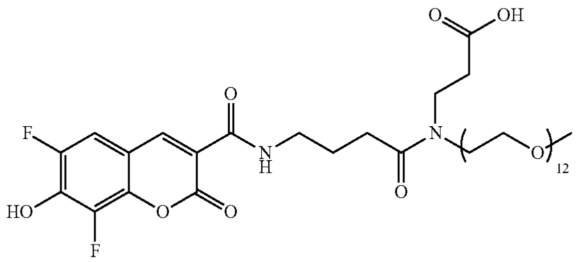

G

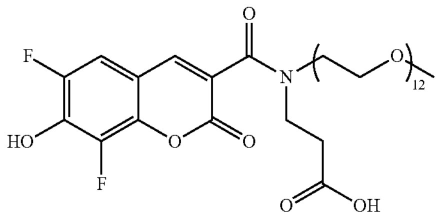

H

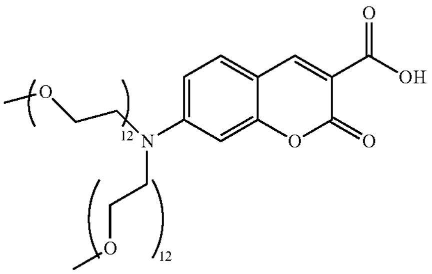

In some instances, the violet excitable donor fluorophore is a pyrene donor fluorophore. Pyrene donor fluorphores are fluorophores that include a polycyclic aromatic hydrocarbon (PAH) having of four fused benzene rings, resulting in a flat aromatic system. The pyrene core may be depicted by the following structure:

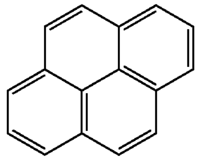 [SMILES: c1cc2ccc3cccc4ccc(c1)c2c34]

Pyrene donore fluorophores of interest include pyrene derivatives. By "pyrene" derivative is meant a molecule comprising the four fused benzene rings of pyrene, wherein one or more of the pyrene carbon atoms is substituted or conjugated to a further moiety. In some instances, the pyrene donor fluorophore present in tandem dyes of the invention is described by the formula:

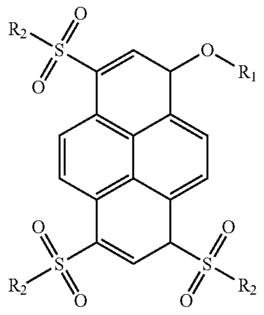

wherein, (a) $R_1$ may be a chemically reactive functional group, such as but not limited to activated ester, activated carbonate, acyl azides, acid halides, or other reactive groups, e.g., that include acrylamides, alkyl and arylazides, alkynes and constrained cyclic alkynes, anhydrides, halides, sulfonate esters, amines, alcohols, carboxylic acids, haloacetamides, isothiocyanates and isocyanates, or a conjugate of such a reactive group and additional moiety, e.g., R short alkyl chains, or cyclic rings with or without heteroatoms such as nitrogen, oxygen, sulfur, phosphorus, which ring may or may not be substituted; and (b) $R_2$ are hydrogen atoms, or short alkyl chains, or cyclic rings with or without heteroatoms such as nitrogen, oxygen, sulfur, phosphorus, or water-solubilizing groups (WSGs).

Examples of pyrene donor fluorophores of embodiments of the invention include, but are not limited to:

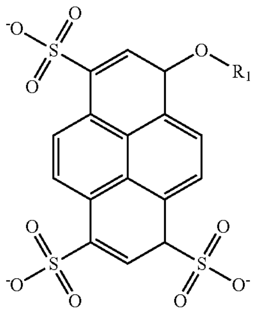

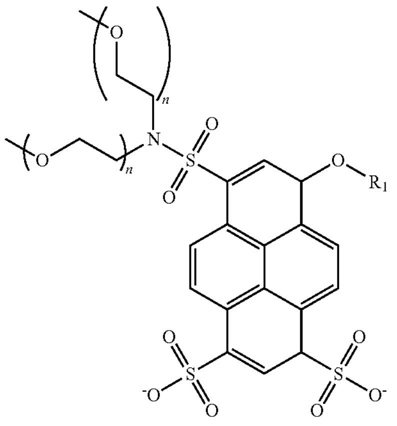

-continued

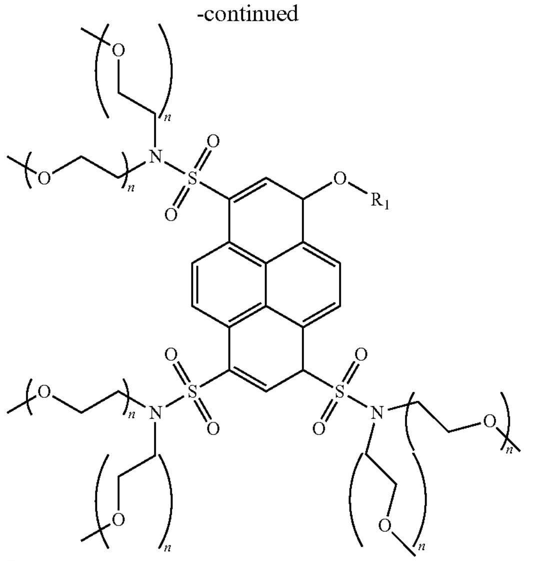

$R_1$

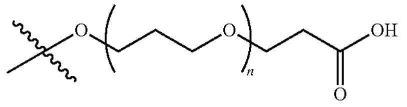

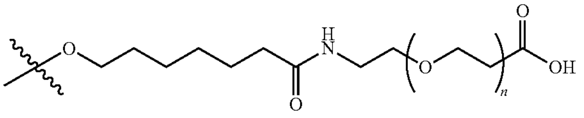

In some instances, the pyrene donor fluorophore present in tandem dyes of the invention is described by the formula:

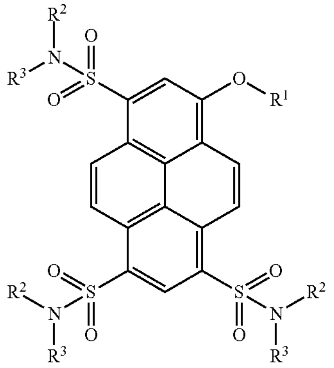

wherein, (a) $R_1$ may be a chemically reactive functional group, such as but not limited to activated ester, activated carbonate, acyl azides, acid halides, or other reactive groups, e.g., that include acrylamides, alkyl and arylazides, alkynes and constrained cyclic alkynes, anhydrides, halides, sulfonate esters, amines, alcohols, carboxylic acids, haloacetamides, isothiocyanates and isocyanates, or a conjugate of such a reactive group and additional moiety, e.g., R short alkyl chains, or cyclic rings with or without heteroatoms such as nitrogen, oxygen, sulfur, phosphorus, which ring may or may not be substituted; and (b) $R_2$ and $R_3$ are hydrogen atoms, or short alkyl chains, or cyclic rings with or without heteroatoms such as nitrogen, oxygen, sulfur, phosphorus, or water-solubilizing groups (WSGs).

In some instances, a pyrene donor fluorophore of a tandem dye of the invention is a pyrene donor fluorophore having the following formula:

I

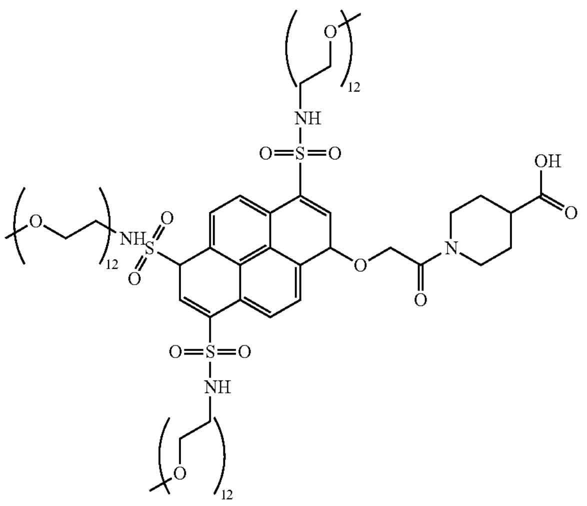

In some instances, the violet excitable donor fluorophore is a triphenyl donor fluorophore. Triphenyl donor fluorophores of interest include donor fluorophores having a triphenyl method core, i.e.:

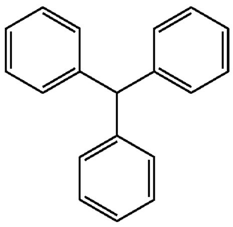 [SMILES: c1ccc(C(c2ccccc2)c2ccccc2)cc1]

In some instances, the triphenyl donor fluorophore is a triarylmethane dye of formula (VI):

(VI)

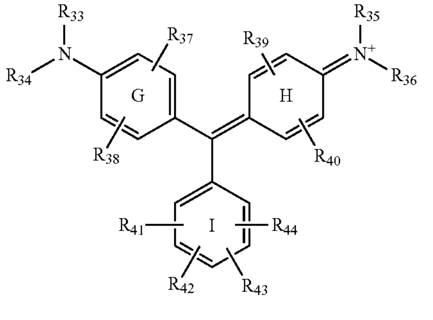

in which formula (VI):

$R_{33}$, $R_{34}$, $R_{35}$ and $R_{36}$, which are identical or different, represent a hydrogen atom or a group chosen from alkyl, optionally substituted aryl and optionally substituted arylalkyl and water solubilizing group;

$R_{37}$, $R_{38}$, $R_{39}$, $R_{40}$, $R_{41}$, $R_{42}$, $R_{43}$ and $R_{44}$, which are identical or different, represent a hydrogen atom or a group chosen from: alkyl; alkoxy, alkylthio; (di) (alkyl) amino; hydroxyl, mercapto; -nitro, nitroso; —$R^o$—C(X)—X'—, $R^o$—X'—C(X)— or R'—X'—C(X)—X"—, with $R^o$ representing a hydrogen atom or an alkyl or aryl group or carboxyl and X, X and X, which are identical or different, representing an oxygen or sulfur atom or alky group or NR, with R representing a hydrogen atom or an alkyl group; or then two adjacent groups $R_{41}$ with $R_{42}$ or $R_{42}$ with $R_{43}$ or $R_{43}$ with $R_{44}$ together form a fused benzo group.

In some instances, a triphenyl donor fluorophore of a tandem dye of the invention is a pyrene donor fluorophore having the following formula:

J

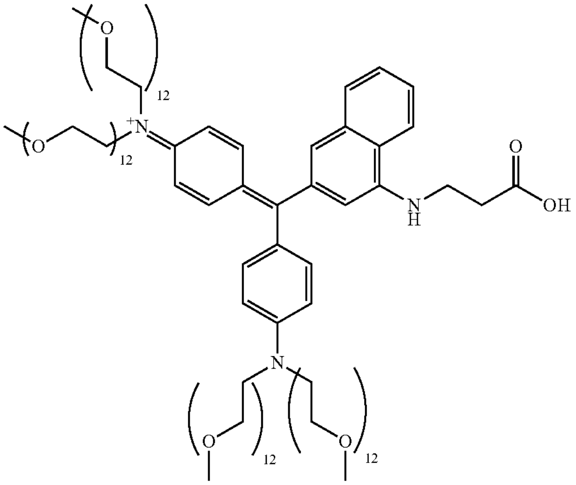

Where desired, the violet excitable donor fluorophores present in tandem dyes of embodiments of the invention may be substituted with one or more water solubilizing groups (WSG), e.g., as defined above.

Acceptor Fluorophores

As summarized above, tandem dyes of the invention include one or more acceptor fluorophores. In some instances, the tandem dyes include a single acceptor fluorophore. In other instances, the tandem dyes include two or more acceptor fluorphores. Any convenient fluorescent dye may be utilized in the polymeric tandem dyes as an acceptor fluorophore. The acceptor fluorophore (e.g., each A) can be a small molecule fluorophore. The acceptor fluorophore (e.g., each A) can be a dye molecule selected from a rhodamine, a perylene, a diimide, a coumarin, a xanthene, a cyanine, a polymethine, a pyrene, a thiazine, an acridine, a dipyrromethene borondifluoride, a napthalimide, a phycobiliprotein, a peridinum chlorophyll protein, conjugates thereof, and combinations thereof. In certain embodiments, the acceptor fluorophore (A) is a cyanine dye, a xanthene dye, a coumarin dye, a thiazine dye or an acridine dye. In some instances, the acceptor fluorophore (A) is selected from DY 431, DY 485XL, DY 500XL, DY 610, DY 640, DY 654, DY 682, DY 700, DY 701, DY 704, DY 730, DY 731, DY 732, DY 734, DY 752, DY 778, DY 782, DY 800, DY 831, Biotium CF 555, Cy 3.5 and diethylamino coumarin. Fluorescent dyes of interest include, but are not limited to, fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, conjugates thereof, and combinations thereof. Lanthanide chelates of interest include, but are not limited to, europium chelates, terbium chelates and samarium chelates. In some embodiments, the polymeric tandem dye includes a multichromophore linked to an acceptor fluorophore selected from Cy3, Cy3.5, Cy5, Cy5.5, Cy7, Alexa488, Alexa 647 and Alexa700. In certain embodiments, the polymeric tandem dye includes a multichromophore linked to an acceptor fluorophore selected from Dyomics dyes (such as DY 431, DY 485XL, DY 500XL, DY 530, DY 610, DY 633, DY 640, DY 651, DY 654, DY 682, DY 700, DY 701, DY 704, DY 730, DY 731, DY 732, DY 734, DY 752, DY 754, DY 778, DY 782, DY 800 or DY 831), Biotium CF 555, Cy 3.5, and diethylamino coumarin. In certain cases, the acceptor fluorophore (A) is selected from fluorescein, 6-FAM, rhodamine, Texas Red, California Red, iFluor594, tetramethylrhodamine, a carboxyrhodamine, carboxyrhodamine 6G, carboxyrhodol, carboxyrhodamine 110, Cascade Blue, Cascade Yellow, coumarin, Cy2®, Cy38, Cy3.58, Cy5®, Cy5.58, Cy76, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimelhoxyfluorescein), NED, ROX (5-(and -6)-carboxy-X-rhodamine), HEX, Lucifer Yellow, Marina Blue, Oregon Green 488, Oregon Green 500, Oregon Green 514, Alexa Fluor®350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY®FL, BODIPY®FL-Br2, BODIPY®530/550, BODIPY®558/568, BODIPY®564/570, BODIPY®576/589, BODIPY®581/591, BODIPY®630/650, BODIPY®650/665, BODIPY®R6G, BODIPY®TMR, BODIPY®TR, conjugates thereof and combinations thereof.

Where desired, the acceptor fluorophores present in tandem dyes of embodiments of the invention may be substituted with one or more water solubilizing groups (WSG), e.g., as defined above.

Polymeric Backbone

As summarized above, tandem fluorescent dyes of embodiments of the invention include a polymeric backbone. In some instances, the polymeric backbone is made up of non-conjugated repeat units having any convenient configuration, such as a linear, branched or dendrimer configuration. The polymeric backbone can be a linear polymer. The polymeric backbone can be branched. In some instances, the dye conjugate includes a plurality of pendant donor chromophore groups each independently linked to a non-conjugated repeat unit of the polymeric backbone. The configuration of pendant groups can be installed during or after synthesis of the polymeric backbone. The incorporation of pendant groups can be with achieved with a random configuration, a block configuration, or in a sequence-specific manner via stepwise synthesis, depending on the particular method of synthesis utilized.

The term "unit" refers to a structural subunit of a polymer. The term unit is meant to include monomers, co-monomers, co-blocks, repeating units, and the like. A "repeating unit" or "repeat unit" is a subunit of a polymer that is defined by the minimum number of distinct structural features that are required for the unit to be considered monomeric, such that when the unit is repeated n times, the resulting structure describes the polymer or a block thereof. In some cases, the polymer may include two or more different repeating units, e.g., when the polymer is a multiblock polymer, a random arrangement of units or a defined sequence, each block may define a distinct repeating unit. It is understood that a variety of arrangements of repeating units or blocks are possible and that in the depicted formula of the polymer backbones described herein any convenient linear arrangements of various lengths can be included within the structure of the overall polymer. It is understood that the polymer may also be represented by a formula in terms of mol % values of each unit in the polymer and that such formula may represent a variety of arrangements of repeat unit, such as random or multiblock polymer or a defined sequence of residues. In some cases, a repeating unit of the polymer includes a single monomer group. In certain instances, a repeating unit of the polymer includes two or more monomer groups, i.e., co-monomer groups, such as two, three, four or more co-monomer groups. The term "co-monomer" or "co-monomer group" refers to a structural unit of a polymer that may itself be part of a repeating unit of the polymer.

The backbone of the tandem dye may have any convenient length. In some cases, the particular number of monomeric repeating units or segments of the chromophore may fall within the range of 2 to 500,000, such as 2 to 100,000, 2 to 30,000, 2 to 10,000, 2 to 3,000 or 2 to 1,000 units or segments, or such as 5 to 100,000, to 100,000, 100 to 100,000, 200 to 100,000, or 500 to 50,000 units or segments. In some instances, the particular number of monomeric repeating units or segments of the backbone may fall within the range of 2 to 1,000, such as 2 to 500, 2 to 100, 3 to 100, 4 to 100, 5 to 100, 6 to 100, 7 to 100, 8 to 100, 9 to 100 or 10 to 100 units or segments. In certain cases, the particular number of monomeric repeating units or segments of the backbone may fall within the range of 2 to 500, such as 2 to 400, 2 to 300, 2 to 200, or 2 to 100 units or segments. In certain cases, the particular number of monomeric repeating units or segments of the backbone may fall within the range of 2 to 100 repeating monomeric units, such as 2 to 90, 2 to 80, 2 to 70, 2 to 60, 2 to 50, 2 to 40, or 2 to 30 units or segments.

The polymeric backbone may have a random configuration of non-conjugated repeat units. The polymeric backbone may include a block or co-block configuration of non-conjugated repeat units. Alternatively, the polymeric backbone may include a particular defined sequence of non-conjugated repeat units, e.g., amino acid residues of a polypeptide sequence. These configurations can be characterized by polymeric segments of repeat units (e.g., as described herein), which segments can themselves be repeated throughout the modular scaffold.

By "non-conjugated" is meant that at least a portion of the repeat unit includes a saturated backbone group (e.g., a group having two or more consecutive single covalent bonds) which precludes pi conjugation or an extended delocalized electronic structure along the polymeric backbone from one repeat unit to the next. It is understood that even though one repeat unit may not be conjugated to an adjacent repeat unit, such a repeat unit may include one or more isolated unsaturated groups including an unsaturated bond (e.g., of an alkenylene group or an alkynylene group) and/or an aryl or heteroaryl group, which groups can be a part of the backbone. In some cases, each repeat unit of the polymeric backbone includes one sidechain including a linked pendant group or a chemo-selective tag for linking to a pendant group.

In certain embodiments of the tandem dyes, the polymeric backbone is a linear polymer. In certain cases, the linear polymer is selected from a peptide, a peptoid, a hydrocarbon polymer, and a PEG polymer. In certain cases, the linear polymer is a peptide. In certain cases, the linear polymer is a peptoid. In certain cases, the polymer is a hydrocarbon polymer. In certain other cases, the polymer is a PEG polymer. Further details regarding polymeric backbones that may be employed in embodiments of the invention are found in PCT application serial no. PCT/US2019/024662 published as WO2019/191482 and PCT application serial no. PCT/US2020/019510 published as WO2020/222894; the disclosures of which applications are herein incorporated by reference.

In certain instances, the tandem dye includes a linear peptide backbone of from 2 to 100 amino acids, such as 2 to 90, 2 to 80, 2 to 70, 2 to 60, 2 to 50, 2 to 40 or 2 to 30 amino acids. In some cases, the linear peptide backbone includes 2 or more amino acids, such as 5 or more, 10 or more, 15 or more, 20 or more, 25 or more, 30 or more, up to a maximum of 100 amino acids. In certain cases, the tandem dye includes a linear peptide backbone of from 5 to 30 amino acids, such as 5 to 25, 5 to 20, 5 to 15, or 5 to amino acids.

Where desired, the polymeric backbones present in tandem dyes of embodiments of the invention may be substituted with one or more water solubilizing groups (WSG), e.g., as defined above.

Additional Aspects of Violet Excitable Tandem Dyes

Violet Excitable polymeric fluorescent tandem dyes of embodiments of the invention may vary. In some instances, polymeric fluorescent tandem dyes of embodiments of the invention include: a polymeric backbone; a plurality of violet excitable pendant donor fluorophores each independently linked to a repeat unit of the polymeric backbone; and one or more pendant acceptor fluorophores linked to a repeat unit of the polymeric backbone, where pendant donor and acceptor fluorophores are in energy transfer relationship. As such, polymeric tandem dyes of embodiments of the invention include one or more pendant donor fluorophores and one or more pendant acceptor fluorophores, configured in energy-receiving proximity to the one or more pendant donor fluorophores, e.g., where both are linked to a common polymeric backbone. In some embodiments, a plurality of pendant donor fluorophores are present and are configured in energy-transferring proximity to a pendant acceptor fluorophore(s), where in some instances the plurality of pendant donor fluorophores ranges from 2 to 20, such as 2 to 15, e.g., 2 to 10. The term "pendant group" refers to a sidechain group that is connected to the backbone but which is not part of the backbone itself. In embodiments of the polymeric tandem dyes, the donor fluorophore is capable of transferring energy to a linked acceptor fluorophore. As such, the subject tandem dyes include a linked acceptor signaling fluorophore in energy-receiving proximity to the donor fluorophore system, i.e., in energy-receiving proximity to at least one linked donor fluorophore. A particular configuration of pendant groups can be determined and controlled by the arrangement of the repeat units of the underlying polymeric backbone (also referred to herein as "modular scaffold" to which the pendant groups are attached. The tandem dyes can include a plurality of water solubilizing groups attached to the scaffold and/or the pendant groups at any convenient locations to provide a water soluble polymeric dye. The polymeric backbone, i.e., modular scaffold, can be composed of repeat units which form a polymeric backbone having sidechain groups to which the pendant groups can be attached. The repeat units can be arranged in a variety of configurations to provide for a tandem dye having desirable spectroscopic properties. The distances and arrangement between sites for covalent attachment of the pendant donor fluorophores and the acceptor fluorophore(s) (when present) can be controlled to provide for desirable energy transfer processes.

As mentioned above, where desired, the polymeric backbone and/or pendant fluorophores (i.e., donor and acceptor fluorophores) may include one or more water solubilizing groups (WSG). In some cases, the WSGs are pendant groups connected directly to the polymeric backbone, e.g., as sidechains of a polymeric backbone. In certain cases, the WSGs are substituent groups attached to a pendant donor fluorophore or pendant acceptor fluorophore. In some instances, each of the pendant donor fluorophore groups are substituted with one or more WSG. As used herein, the terms "water solubilizing group", "water soluble group" and WSG are used interchangeably and refer to a group or substituent that is well solvated in aqueous environments e.g., under physiological conditions, and which imparts improved water solubility upon the molecule to which it is attached. A WSG can increase the solubility of a give polymeric tandem dye in a predominantly aqueous solution, as compared to a control dye which lacks the WSG. The water solubilizing groups may be any convenient hydrophilic group that is well solvated in aqueous environments. A water soluble tandem dye of the present disclosure has solubility under aqueous conditions that makes it especially suitable for application to a variety of biological assays. A variety of water soluble polymer groups can be adapted for use in the WSG of the subject dyes. Any convenient water solubilizing groups (WSG's) may be included in the dyes described herein to provide for increased water-solubility, e.g., as described above.

As summarized above, polymeric fluorescent tandem dyes of embodiments of the invention include a plurality of pendant donor fluorophores and one or more pendant acceptor fluorophores. In some instances, the number of donor fluorophores exceeds the number of acceptor fluorophores. In certain embodiments of the subject tandem dyes, the ratio of donor fluorophores to acceptor fluorophores is selected from 5:1, 6:1, 7:1, 8:1, 9:1, 10:1, and 20:2. In certain cases, the ratio of donor fluorophores to acceptor fluorophores is 5:1. In certain cases, the ratio of donor fluorophores to acceptor fluorophores is 6:1. In certain cases, the ratio of donor fluorophores to acceptor fluorophores is 7:1. In certain cases, the ratio of donor fluorophores to acceptor fluorophores is 8:1. In certain cases, the ratio of donor fluorophores to acceptor fluorophores is 9:1. In certain cases, the ratio of donor fluorophores to acceptor fluorophores is 10:1.

As mentioned above, in polymeric fluorescent tandem dyes of the invention, pendant donor and acceptor fluorophores are in energy transfer relationship. As such, in embodiments of the invention, excitation of the donor can lead to energy transfer to, and emission from, the covalently attached acceptor signaling fluorophore. Mechanisms for energy transfer between the donor chromophores to a linked acceptor signaling fluorophore include, for example, resonant energy transfer (e.g., Förster (or fluorescence) resonance energy transfer, FRET), quantum charge exchange (Dexter energy transfer) and the like. These energy transfer mechanisms can be relatively short range; that is, close proximity of chromophores of the light harvesting multichromophore system to each other and/or to an acceptor fluorophore provides for efficient energy transfer. Under conditions for efficient energy transfer, amplification of the emission from the acceptor fluorophore can occur where the emission from the luminescent acceptor fluorophore is more intense when the incident light (the "pump light") is at a wavelength which is absorbed by, and transferred from, the chromophores of the light harvesting chromophore than when the luminescent acceptor fluorophore is directly excited by the pump light. By "efficient" energy transfer is meant 10% or more, such as 20% or more or 30% or more, 40% or more, 50% or more, of the energy harvested by the donor chromophores is transferred to the acceptor. By "amplification" is meant that the signal from the acceptor fluorophore is 1.5× or greater when excited by energy transfer from the donor light harvesting chromophore system as compared to direct excitation of the acceptor fluorophore with incident light of an equivalent intensity. The signal may be measured using any convenient method. In some cases, the 1.5× or greater signal refers to an intensity of emitted light. In certain cases, the 1.5× or greater signal refers to an increased signal to noise ratio. In certain embodiments of the tandem dye, the acceptor fluorophore emission is 1.5 fold greater or more when excited by the chromophore as compared to direct excitation of the acceptor fluorophore with incident light, such as 2-fold or greater, 3-fold or greater, 4-fold or greater, 5-fold or greater, 6-fold or greater, 8-fold or greater, 10-fold or greater, 20-fold or greater, 50-fold or greater, 100-fold or greater, or even greater as compared to direct excitation of the acceptor fluorophore with incident light.

The tandem dyes of embodiments of the invention may be of any convenient molecular weight (MW). In some cases, the MW of the tandem dye may be expressed as an average molecular weight. In some instances, the tandem dye has an average molecular weight in the range of 500 to 500,000, such as from 1,000 to 100,000, from 2,000 to 100,000, from 10,000 to 100,000 or even an average molecular weight in the range of 50,000 to 100,000 daltons. In some instances, the polymeric fluorescent dyes have a molecular weight ranging from 5 to 75 kDa, such as 10 to 50 kDa, such as 15 to kDa.

As summarized above, tandem dyes of embodiments of the invention are violet excitable tandem dyes. As such, violet excitable tandem dyes are dyes that may be excited by violet light, e.g., violet light provided by a violet laser. In some instances, violet excitable tandem dyes are excitable by light having a wavelength ranging from 350 to 450 nm. The excitation maximum of violet excitable tandem dyes of the invention may vary, and in some embodiments ranges from 375 to 425 nm, such as 390 to 410 nm, e.g., 400 to 410 nm.

In some instances, the tandem dye exhibits an effective Stokes shift of 100 nm or more, such as 110 nm or more, 120 nm or more, 130 nm or more, 140 nm or more, 150 nm or more, 160 nm or more, 170 nm or more, 180 nm or more, 190 nm or more, 200 nm or more, 250 nm or more when the light harvesting chromophore is directly excited with incident light. In some cases, the effective Stokes shift of the tandem dye is up to about 300 nm such as 100-300 nm, 100-250 nm or 100-200 nm.

The emission of the polymeric tandem dye can have a quantum yield of 0.03 or more, such as a quantum yield of 0.04 or more, 0.05 or more, 0.06 or more, 0.07 or more, 0.08 or more, 0.09 or more, 0.1 or more, 0.15 or more, 0.2 or more, 0.3 or more or even more. In some instances, the polymeric tandem dye has an extinction coefficient of $5\times10^5$ $cm^{-1}$ $M^{-1}$ or more, such as $6\times10^5$ $cm^{-1}$ $M^{-1}$ or more, $7\times10^5$ $cm^{-1}$ $M^{-1}$ or more, $8\times10^5$ $cm^{-1}$ $M^{-1}$ or more, $9\times10^5$ $cm^{-1}$ $M^{-1}$ or more, such as $1\times10^6$ $cm^{-1}$ $M^{-1}$ or more, $1.5\times10^6$ $cm^{-1}$ $M^{-1}$ or more, $2\times10^6$ $cm^{-1}$ $M^{-1}$ or more, $2.5\times10^6$ $cm^{-1}$ $M^{-1}$ or more, $3\times10^6$ $cm^{-1}$ $M^{-1}$ or more, $4\times10^6$ $cm^{-1}$ $M^{-1}$ or more, $5\times10^6$ $cm^{-1}$ $M^{-1}$ or more, $6\times10^6$ $cm^{-1}$ $M^{-1}$ or more, $7\times10^6$ $cm^{-1}$ $M^{-1}$ or more, or $8\times10^6$ $cm^{-1}$ $M^1$ or more. In some embodiments, the polymeric tandem dye has a molar extinction coefficient of $5\times10^5$ $M^{-1}$ $cm^{-1}$ or more. In certain embodiments, the tandem dye has a molar extinction coefficient of $1\times10^6$ $M^{-1}$ $cm^{-1}$ or more.

In embodiments, the subject tandem dyes provide for fluorescence emissions from acceptor fluorophores that are brighter than the emissions which are possible from such fluorescent dyes in isolation. The emission of the polymeric tandem dye can have a brightness of 50 $mM^{-1}$ $cm^{-1}$ or more, such as 60 $mM^{-1}$ $cm^{-1}$ or more, 70 $mM^{-1}$ $cm^{-1}$ or more, 80 $mM^{-1}$ $cm^{-1}$ or more, 90 $mM^{-1}$ $cm^{-1}$ or more, 100 $mM^{-1}$ $cm^{-1}$ or more, 150 $mM^{-1}$ $cm^{-1}$ or more, 200 $mM^{-1}$ $cm^{-1}$ or more, 250 $mM^{-1}$ $cm^{-1}$ or more, 300 $mM^{-1}$ $cm^{-1}$ or more, or even more. In certain instances, the emission of the tandem dye has a brightness that is at least 5-fold greater than the brightness of a directly excited acceptor fluorophore, such as at least 10-fold greater, at least 20-fold greater, at least 30-fold greater, at least 50-fold greater, at least 100-fold greater, at least 300-fold greater, or even greater than the brightness of a directly excited acceptor fluorophore.

In addition to attributes such as described above, tandem dyes of embodiments of the invention may have one or more additional desirable spectroscopic properties, such as a particular emission maximum wavelength, extinction coefficient, quantum yield, and the like.

A variety of emission profiles which depend on a variety of factors such as the selected co-monomers, linking groups, substituents and linked acceptor fluorophores of which the tandem dyes are composed. In some embodiments, the tandem dye has an emission maximum wavelength in the range of 425 to 900 nm, such as in the range of 450 nm to 900 nm, 475 nm to 900 nm, or 500 nm to 900 nm.

In some embodiments, the polymeric tandem dyes can include a segment of the formula (Ia):

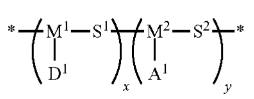

(Ia)

wherein:

each $M^1$ and $M^2$ is independently an unsaturated co-monomer (e.g., an amino acid residue);

each $S^1$ and $S^2$ is independently an optional non-conjugated spacer unit;

each $D^1$ is independently a pendant violet excitable donor fluorophore (e.g., as described herein) linked to $M^1$;

each $A^1$ is independently an acceptor fluorophore linked to $M^2$;

x is 75 mol % or more; and y is 25 mol % or less.

The first ($M^1$-$S^1$) and second repeat units ($M^2$-$S^2$) can be arranged in a random or co-block configuration. In certain cases of formula (Ia), the $D^1$ pendant groups of the first repeat units include two or more (e.g., two or three) distinct types of pendant light absorbing chromophores that together provide a light harvesting multichromophore system. In certain instances of formula (Ia), the $D^1$ pendant groups of the first repeat units are all the same.

In some instances of formula (Ia), x is 80 mol % or more, such as 85 mol % or more, 90 mol % or more, 95 mol % or more, 96 mol % or more, 97 mol % or more, 98 mol % or more, or 99 mol % or more. In some instances of formula (Ia), y is 20 mol % or less, such as 15 mol % or less, 10 mol % or less, 5 mol % or less, 4 mol % or less, 3 mol % or less, 2 mol % or less, 1 mol % or less.

In some instances, the polymeric tandem dye includes a segment of formula (IIa):

(IIa)

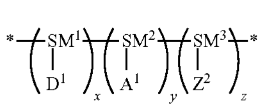

wherein:

the polymeric backbone of non-conjugated repeat units comprises $SM^1$, $SM^2$ and $SM^3$ co-monomers that are each independently a non-conjugated co-monomer;

each $D^1$ is independently a pendant violet excitable donor fluorophore (e.g., as described herein) linked to $SM^1$;

each $A^1$ is independently an acceptor fluorophore linked to $SM^2$;

each $Z^2$ is an optional sidechain group linked to $SM^3$;

x is 50 mol % or more; and y+z is 50 mol % or less.

$Z^2$ can be absent or any convenient sidechain group, such as a light absorbing chromophore, a chemoselective tag, a linker, a linked biomolecule, a acceptor fluorophore, a WSG (e.g., as described in PCT Application Serial No. PCT/US2019/024662 published as WO 2019/191482, the disclosure of which is herein incorporated by reference), etc. In certain cases of formula (IIa), $SM^3$ is a spacer co-monomer where $Z^2$ is absent. In certain instances of formula (IIa), $SM^3$ is a co-monomer including a $Z^2$ group that is a second pendant light absorbing chromophore, where each $D^1$ and each $Z^2$ together provide a light harvesting multichromophore system. In some cases, $SM^3$ is a co-monomer including a second chemoselective tag ($Z^2$), e.g., a protected functional group or a tag that is orthogonal to $Z^1$ that provides for the selective installation of a moiety of interest.

In certain cases of formula (IIa), x is 60 mol % or more, such as 65 mol % or more, 70 mol % or more, 75 mol % or more, 80 mol % or more, 85 mol % or more, 90 mol % or more, 95 mol % or more, or even more. In certain instances of formula (IIa), y+z is 40 mol % or less, such as 30 mol % or less, 25 mol % or less, 20 mol % or less, 15 mol % or less, 10 mol % or less, 5 mol % or less, or even less. In certain instances of formula (IIa), y is at least 1 mol % and 25 mol % or less, such as 20 mol % or less, 15 mol % or less, 10 mol % or less, 5 mol % or less, or even less. In certain instances of formula (IIa), z is at least 1 mol % and 10 mol % or less, such as 5 mol % or less, or even less.

In some instances, the polymeric tandem dye includes a segment of formula (IIIa):

(IIIa)

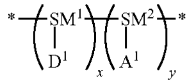

wherein:

the polymeric backbone of non-conjugated repeat units comprises $SM^1$ and $SM^2$ co-monomers that are each independently a non-conjugated co-monomer;

each $D^1$ is independently a pendant violet excitable donor fluorophore (e.g., as described herein) linked to $SM^1$;

each $A^1$ is independently an acceptor fluorophore linked to $SM^2$;

x is 75 mol % or more; and y is 25 mol % or less.

In certain embodiments of formula (IIIa), $SM^1$ and $SM^2$ are each independently a saturated non-conjugated co-monomer, e.g., a co-monomer providing only single covalent C—C bonds. In some embodiments of formula (IIIa), $SM^1$ and $SM^2$ are each independently a partially saturated non-conjugated co-monomer, e.g., a co-monomer providing an isolated double C═C covalent bond in a backbone of saturated covalent bonds. The first and second repeat units ($SM^1$ and $SM^2$) of formula (IIIa) can be arranged in a random configuration, a block or co-block configuration, or in a particular sequence. In certain cases of formula (IIIa), the $D^1$ pendant groups of the $SM^1$ include two or more (e.g., two or three) distinct types of pendant light absorbing chromophores that together provide a light harvesting multichromophore system. In certain instances of formula (IIIa), the $D^1$ pendant groups of the first repeat units are all the same.

In some instances of formula (IIIa), x is 80 mol % or more, such as 85 mol % or more, 90 mol % or more, 95 mol % or more, 96 mol % or more, 97 mol % or more, 98 mol % or more, or 99 mol % or more. In some instances of formula (IIIa), y is 20 mol % or less, such as 15 mol % or less, 10 mol % or less, 5 mol % or less, 4 mol % or less, 3 mol % or less, 2 mol % or less, 1 mol % or less.

In certain instances, the polymeric tandem dye is of formula (IVa):

(IVa)

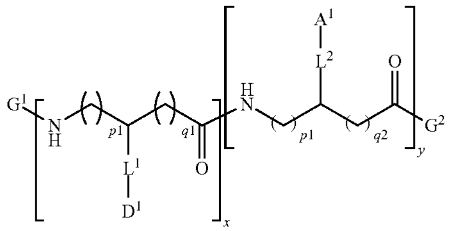

wherein:

each $D^1$ is independently a pendant violet excitable donor fluorophore (e.g., as described herein);

each $A^1$ is independently an acceptor fluorophore;

each $L^1$ and $L^2$ are independently a linker;

$p_1$ and $q_1$ are independently 0 or 1 wherein $p_1+q_1 \leq 1$;

$p_2$ and $q_2$ are independently 0 or 1 wherein $p_1+q_1 \leq 1$;

x is 75 mol % or more;

y is 25 mol % or less; and $G^1$ and $G^2$ are each independently selected from a terminal group, a polymer segment, a light absorbing (e.g., donor) chromophore group, an acceptor fluorophore, a linker and a linker to a specific binding member, e.g., as described above.

In some embodiments of formula (IVa), $p_1$ and $p_2$ are each 0 and $q_1$ and $q_2$ are each 1 (e.g., β3-amino acid residues). In some embodiments of formula (IVa), $p_1$ and $p_2$ are each 1 and $q_1$ and $q_2$ are each 0 (e.g., β2-amino acid residues). In some cases, $p_1$, $p_2$, $q_1$ and $q_2$ are each 0 and the polymeric tandem dye is of formula (Va):

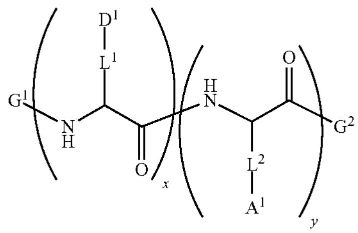

wherein:

each $D^1$ is independently a pendant violet excitable donor fluorophore (e.g., as described herein);

each $A^1$ is independently an acceptor fluorophore;

$L^1$ and $L^2$ are each independently a linker;

x is 75 mol % or more;

y is 25 mol % or less; and $G^1$ and $G^2$ are each independently selected from a terminal group, a polymer segment, a light absorbing (e.g., donor) chromophore group, a linker and a linker to a specific binding member, e.g., as described above. It is understood that the tandem dyes described by formula (Va) include any convenient arrangements of co-monomers in a defined linear sequence, which have in total the defined mol % ratios of x and y. In some cases, the $A^1$ containing co-monomers are spaced throughout the sequence of the polymeric backbone and as such are always flanked on both sides by one or more D1 containing co-monomers.

In certain instances of formula (Va), the polymeric tandem dye includes a segment of formula (VIa):

(VIa)

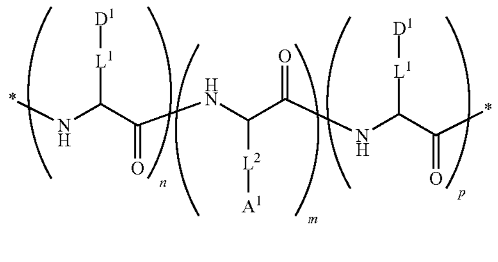

wherein:

each $D^1$ is independently a pendant violet excitable donor fluorophore (e.g., as described herein);

each $A^1$ is independently an acceptor chromophore;

each $L^1$ and $L^2$ are independently a linker;

n and p are each independently an integer from 1 to 20 wherein n+p≥2; and m is 1 or 2.

In some cases of formula (VIa), n and p are each independently 1 to 10 such as 2 to 20, 3 to 10 or 3 to 6. In some instances of formula (VIa), n+p is an integer from 2 to 20, such as 3 to 20, 4 to 20, 5 to 20, 5 to 15 or 5 to 12. In certain embodiments of formula (VIa), m is 1.

The subject polymeric tandem dyes can include multiple segments of formula (VIa) where each segment includes one isolated $A^1$ containing co-monomers flanked by blocks of $D^1$ containing co-monomers. In some cases, the multichromophore includes two or more segments of formula (VIa) located directed adjacent to each other to provide two isolated $A^1$ containing co-monomers separated by a block of 2-20 $D^1$ containing co-monomers, such as a block of 3 to 20, 4 to 20, 5 to 20, 5 to 15 or 5 to 12 $D^1$ containing co-monomers. As such, in certain embodiments, the polymeric tandem dye includes q segments of a block copolymer and is of formula (VIIa):

(VIIa)

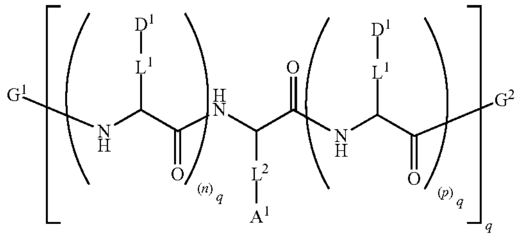

wherein: each $(n)_q$ and each $(p)_q$ is independently an integer from 1 to 20, wherein for each of the q segments $(n)_q+(p)_q \geq 3$; and q is an integer from 1 to 100.

In certain embodiments, the polymeric tandem dye has the formula (VIIa):

(VIIIa)

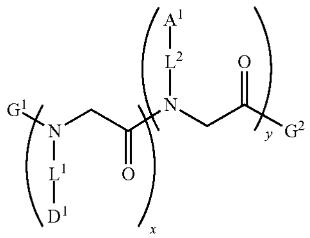

wherein each $D^1$ is independently a pendant violet excitable donor fluorophore (e.g., as described herein);

each $A^1$ is independently an acceptor chromophore;

each $L^1$ and $L^2$ is independently a linker;

x is 75 mol % or more;

y is 25 mol % or less; and $G^1$ and $G^2$ are each independently selected from a terminal group, a polymer segment, a donor chromophore group, a linker and a linker to a specific binding member, e.g., as described above.

In certain embodiments, the polymeric tandem dye has the formula (IXa):

(IXa)

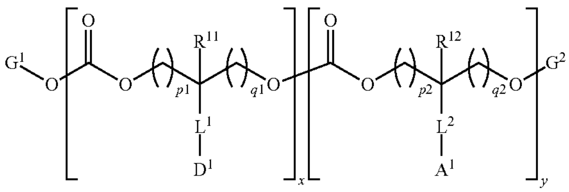

wherein:

each $D^1$ is independently a pendant violet excitable donor fluorophore (e.g., as described herein);

each $A^1$ is independently an acceptor fluorophore;

each $L^1$ and $L^2$ is independently a linker;

x is 75 mol % or more;

y is 25 mol % or less; and $G^1$ and $G^2$ are each independently selected from the group consisting of a terminal group, a polymer segment, a donor chromophore group, an acceptor fluorophore, a linker and a linker to a specific binding member, e.g., as describe above.

In some instances of formulae (IVa), (Va), (XIIIa) and (IXa), x is 80 mol % or more, such as 85 mol % or more, 90 mol % or more, 95 mol % or more, 96 mol % or more, 97 mol % or more, 98 mol % or more, or 99 mol % or more. In some instances of formula (IV), (V), (XIII) and (IX), y is 20 mol % or less, such as 15 mol % or less, 10 mol % or less, mol % or less, 4 mol % or less, 3 mol % or less, 2 mol % or less, 1 mol % or less.

In certain embodiments, the polymeric tandem dye has the formula (Xa):

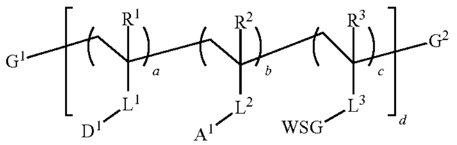

wherein:

each $D^1$ is independently a pendant violet excitable donor fluorophore (e.g., as described herein);

each $A^1$ is independently an acceptor fluorophore;

each $L^1$, $L^2$ and $L^3$ is independently a linker;

a, b and c are mol % values for each co-monomer;

d represents the total polymerization or average length of the polymer (e.g., d is 2-1000, such as 2-500, 2-200, 2-100 or 2-50);

WSG is a water solubilizing group (e.g., as described above and in PCT application serial no. PCT/US2019/024662 published as WO 2019/191482, the disclosure of which is herein incorporated by reference); and $G^1$ and $G^2$ are each independently selected from the group consisting of a terminal group, a polymer segment, a donor chromophore group, an acceptor fluorophore, a linker and a linker to a specific binding member, e.g., as described above.

In some instances of formula (Xa), c=0. In some instances of formula (Xa), a>0 and b>0. In some instances of formula (Xa), a is 80 mol % or more, such as 85 mol % or more, 90 mol % or more, 95 mol % or more, 96 mol % or more, 97 mol % or more, 98 mol % or more, or 99 mol % or more. In some instances of formula (Xa), b is 20 mol % or less, such as 15 mol % or less, 10 mol % or less, 5 mol % or less, 4 mol % or less, 3 mol % or less, 2 mol % or less, 1 mol % or less. In some instances of formula (Xa), a is 65-95 mol %, b is 5-35 mol % and c is 0-30 mol %, where a+b+c=100%.

Any convenient end groups (e.g., $G^1$ and $G^2$) may be utilized at the terminals of the tandem fluorescent dyes. As used herein, the terms "end group" and "terminal group" are used interchangeably to refer to the groups located at the terminals of the polymeric structure of the tandem dye, e.g., as described herein. $G^1$ and $G^2$ groups of interest include, but are not limited to H, chemoselective groups, a linker (which may or may not be activated, and a linker conjugated to a specific binding member, e.g., as described above. It is understood that linkers located at the $G^1$ and/or $G^2$ positions of the polymeric backbone may be selected so as to be orthogonal to any other linkers including chemoselective tags (e.g., as described herein) that may be present at a sidechain of the tandem dye. In certain embodiments, an amino functional group or derivative thereof is included at $G^1$ and/or $G^2$. In certain embodiments, a carboxylic acid functional group or derivative thereof is included at $G^1$ and/or $G^2$.

In some embodiments of the formulae described herein, at least one of $G^1$ and $G^2$ is $-L^6-Z^4$ where $L^6$ is a linker (e.g., as described herein) and $Z^4$ is a specific binding member (e.g., as described herein). In some embodiments of formulae described herein, at least one of $G^1$ and $G^2$ is $-L^6-Z^3$ where $L^6$ is a linker (e.g., as described herein) and $Z^3$ is a chemoselective tag (e.g., as described herein). Any convenient chemoselective tag and conjugation chemistries can be adapted for use in the subject light harvesting chromophores. Chemoselective tags of interest include, but are not limited to, amine, active ester, maleimide, thiol, sulfur (VI) fluoride exchange chemistry (SuFEX), sulfonyl fluoride, Diers Alder cycloaddition click reagents and click chemistry, tetrazine, transcyclooctene, aldehyde, alkoxylamine, alkynes, cyclooctynes, azide, and the like. In some instances, $Z^3$ is selected from the group consisting of carboxylic acid, active ester (e.g., N-hydroxy succinimidyl ester (NHS) or sulfo-NHS), amino, maleimide, iodoacetyl and thiol. In certain embodiments of formulae described herein, at least one of $G^1$ and $G^2$ is described by the following structure:

*—Ar-L-Z where Ar is a π-conjugated aryl group, L is a linker and Z is a chemoselective tag or a specific binding member. In some cases, the L-Z group can be connected directed to a terminal co-monomer. In certain embodiments of formulae described herein, at least one of $G^1$ and $G^2$ is described by the following structure:

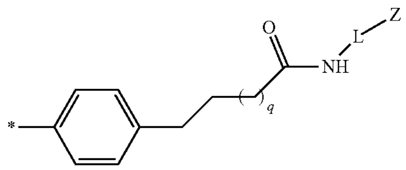

wherein:

q is 0 or an integer from 1-12;

L is an optional linker; and

Z is a chemoselective tag or a specific binding member.

Further details regarding WSG groups that may be found in tandem dyes of embodiments of the invention are found in PCT application serial no. PCT/US2019/

024662 published as WO 2019/191482, the disclosure of which is herein incorporated by reference.

A representative violet excitable polymeric fluorescent tandem dye according to an embodiment of the invention has the following structure:

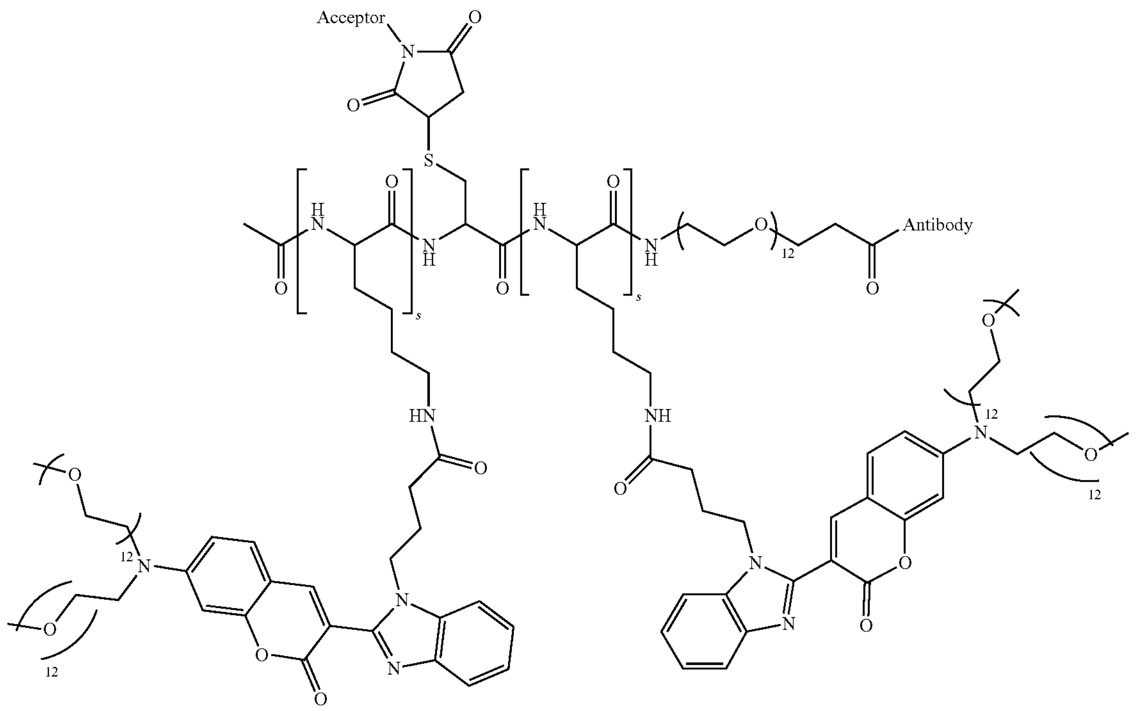

As can be seen, the above violet excitable polymeric tandem dye includes a sixteen violet excitable donor coumarin fluorophores flanking a single acceptor fluorophore (eight donors on each side), where the tandem dye is conjugated to an antibody for specific binding to a target analyte of interest. The violet excitable coumarin donor fluorophores are substituted with PEG water-solubilizing groups and the peptide backbone includes a water-solubilizing PEG spacer between the peptide and the terminally linked antibody.

Methods

Aspects of the invention include methods of evaluating a sample for the presence of a target analyte. Aspects of the methods include contacting a sample with a labeled specific binding member that specifically binds the target analyte to produce an assay composition comprising the labeled specific binding member contacted sample. The labeled specific binding member employed in embodiments of methods of the invention includes a specific binding member conjugated to a violet excitable polymeric fluorescent tandem dye, e.g., as described above. In the following section, the target analyte may be a target molecule of interest or reagent, e.g., primary antibody, bound to the target molecule, depending on whether the labeled specific binding member is employed as a primary or secondary label. Any convenient method may be used to contact the sample with a labeled specific binding member that specifically binds to the target analyte to produce the assay composition. In some instances, the sample is contacted with the labeled specific binding member under conditions in which the labeled specific binding member specifically binds to the target analyte, if present.

For specific binding of the labeled specific binding member with the target analyte, an appropriate medium may be used that maintains the biological activity of the components of the sample and the signal domain antibody. The medium may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target analyte, including dMEM, HBSS, dPBS, RPMI, Iscove's medium, etc., in some cases supplemented with fetal calf serum or human platelet lysate. The final components of the medium, which may be a solution, may be selected depending on the components of the sample which are included. The temperature at which specific binding of the labeled specific binding member to the target analyte takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the biological activity of the specific binding member and/or the target analyte. In certain instances, the temperature is 25° C., 30° C., 35° C. or 37° C. In certain cases, the temperature at which specific binding takes place is room temperature (e.g., 25° C.), 30° C., 35° C. or 37° C. Any convenient incubation time for specific binding may be selected to allow for the formation of a desirable amount of binding complex, and in some instances, may be 1 minute (min) or more, such as 2 min or more, 10 min or more, 30 min or more, 1 hour or more, 2 hours or more, or even 6 hours or more.

Any convenient specific binding members may be utilized in the labeled specific binding members employed in methods of the invention. Specific binding members of interest include, but are not limited to, those specific binding members that specifically bind cell surface proteins of a variety of cell types, including but not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus cells (e.g., HIV cells) NK cells, macrophages, monocytes, fibroblasts, epithelial cells, endothelial cells, and erythroid cells. Target cells of interest include cells that have a convenient cell surface marker or antigen that may be captured by a convenient specific binding member conjugate. In some embodiments, the target cell is selected from HIV containing cell, a Treg cell, an antigen-specificT-cell populations, tumor cells or hematopoetic progenitor cells (CD34+) from whole blood, bone marrow or cord blood. Any convenient cell surface proteins or cell markers may be targeted for specific binding to the conjugates employed in the subject methods. In some embodiments, the target cell includes a cell surface marker selected from a cell receptor and a cell surface antigen. In some cases, the target cell may include a cell surface antigen such as CD11b, CD123, CD14, CD15, CD16, CD19, CD193, CD2, CD25, CD27, CD3, CD335, CD36, CD4, CD43, CD45RO, CD56, CD61, CD7, CD8, CD34, CD1c, CD23, CD304, CD235a, T cell receptor alpha/beta, T cell receptor gamma/delta, CD253, CD95, CD20, CD105, CD117, CD120b, Notch4, Lgr5 (N-Terminal), SSEA-3, TRA-1-60 Antigen, Disialoganglioside GD2 and CD71.

Any convenient targets may be selected for evaluation utilizing the subject methods. Targets of interest include, but are not limited to, a nucleic acid, such as an RNA, DNA, PNA, CNA, HNA, LNA or ANA molecule, a protein, such as a fusion protein, a modified protein, such as a phosphorylated, glycosylated, ubiquitinated, SUMOylated, or acetylated protein, or an antibody, a peptide, an aggregated biomolecule, a cell, a small molecule, a vitamin and a drug molecule. As used herein, the term “a target protein” refers to all members of the target family, and fragments thereof. The target protein may be any protein of interest, such as a therapeutic or diagnostic target, including but not limited to: hormones, growth factors, transcription factor, receptors, enzymes, cytokines, osteo-inductive factors, colony stimulating factors and immunoglobulins. The term “target protein” is intended to include recombinant and synthetic molecules, which can be prepared using any convenient recombinant expression methods or using any convenient synthetic methods, or purchased commercially. In some embodiments, the polymeric dye conjugates include an antibody or antibody fragment. Any convenient target analyte that specifically binds an antibody or antibody fragment of interest may be targeted in the subject methods.

In some embodiments, the target analyte is associated with a cell. In certain instances, the target analyte is a cell surface marker of the cell. In certain cases, the cell surface marker is selected from the group consisting of a cell receptor and a cell surface antigen. In some instances, the target analyte is an intracellular target, and the method further includes treating the cell so as to provide access of the labeled specific binding member to the intracellular target, e.g., by permeabilizing or lysing the cell. As such, a labeled specific binding member employed in methods of the invention may target a cell surface or intracellular antigen. Alternatively, a labeled specific binding member employed in methods of the invention may target a primary antibody that in turn specifically binds to a target cell surface or intracellular antigen.

In some embodiments, the sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue. In some cases, the sample includes hematopoetic progenitor cells (e.g., CD34+ cells) in whole blood, bone marrow or cord blood. In certain embodiments, the sample includes tumor cells in peripheral blood. In certain instances, the sample is a sample including (or suspected of including) viral cells (e.g., HIV).

The labeled specific binding members find use in the subject methods, e.g., for labeling a target cell, particle, target or analyte with a polymeric tandem fluorescent dye. For example, labeled specific binding members find use in labeling cells to be processed (e.g., detected, analyzed, and/or sorted) in a flow cytometer. The labeled specific binding members may include specific binding members, e.g., antibodies or binding fragments thereof, that specifically bind to, e.g., cell surface proteins of a variety of cell types (e.g., as described herein). The labeled specific binding members may be used to investigate a variety of biological (e.g., cellular) properties or processes such as cell cycle, cell proliferation, cell differentiation, DNA repair, T cell signaling, apoptosis, cell surface protein expression and/or presentation, and so forth. Labelled specific binding members may be used in any application that includes (or may include) antibody-mediated labeling of a cell, particle or analyte.

Aspects of the methods include assaying the assay composition, i.e., labeled specific binding member contacted sample, for the presence of a labeled specific binding member-target analyte binding complex to evaluate whether the target analyte is present in the sample. Once the sample has been contacted with the labeled specific binding member, any convenient method may be utilized in assaying the assay composition that is produced for the presence of a labeled specific binding member-target analyte binding complex. The labeled specific binding member-target analyte binding complex is the binding complex that is produced upon specific binding of the labeled specific binding member to the target analyte (or primary binding member, e.g., primary antibody, to the target antigen depending on the embodiment), if present. Assaying the assay composition may include detecting a fluorescent signal from the binding complex, if present. In some cases, the assaying includes a separating step where the target analyte, if present, is separated from the sample. A variety of methods can be utilized to separate a target analyte from a sample, e.g., via immobilization on a support. Assay methods of interest include, but are not limited to, any convenient methods and assay formats where pairs of specific binding members such as avidin-biotin or hapten-anti-hapten antibodies find use, are of interest. Methods and assay formats of interest that may be adapted for use with the subject compositions include, but are not limited to, flow cytometry methods, in-situ hybridization methods, enzyme-linked immunosorbent assays (ELISAs), western blot analysis, magnetic cell separation assays and fluorochrome purification chromatography.

In certain embodiments, the method further includes contacting the sample with a second specific binding member that specifically binds the target analyte. In certain instances, the second specific binding member is support bound. Any convenient supports may be utilized to immobilize a component of the subject methods (e.g., a second specific binding member). In certain instances, the support is a particle, such as a magnetic particle. In some instances, the second specific binding member and the polymeric dye conjugate produce a sandwich complex that may be isolated and detected, if present, using any convenient methods. In some embodiments, the method further includes flow cytometrically analyzing the polymeric dye conjugate-target analyte binding complex, i.e., a fluorescently labelled target analyte. Assaying for the presence of a labeled specific binding member—target analyte binding complex may provide assay results (e.g., qualitative or quantitative assay data) which can be used to evaluate whether the target analyte is present in the sample.

Any convenient supports may be utilized in the subject methods to immobilize any convenient component of the methods, e.g., labelled specific binding member, target, secondary specific binding member, etc. Supports of interest include, but are not limited to: solid substrates, where the substrate can have a variety of configurations, e.g., a sheet, bead, or other structure, such as a plate with wells; beads, polymers, particle, a fibrous mesh, hydrogels, porous matrix, a pin, a microarray surface, a chromatography support, and the like. In some instances, the support is selected from the group consisting of a particle, a planar solid substrate, a fibrous mesh, a hydrogel, a porous matrix, a pin, a microarray surface and a chromatography support. The support may be incorporated into a system that it provides for cell isolation assisted by any convenient methods, such as a manually-operated syringe, a centrifuge or an automated liquid handling system. In some cases, the support finds use in an automated liquid handling system for the high throughput isolation of cells, such as a flow cytometer.

In some embodiments of the method, the separating step includes applying an external magnetic field to immobilize a magnetic particle. Any convenient magnet may be used as a source of the external magnetic field (e.g., magnetic field gradient). In some cases, the external magnetic field is generated by a magnetic source, e.g. by a permanent magnet or electromagnet. In some cases, immobilizing the magnetic particles means the magnetic particles accumulate near the surface closest to the magnetic field gradient source, i.e. the magnet.

The separating may further include one or more optional washing steps to remove unbound material of the sample from the support. Any convenient washing methods may be used, e.g., washing the immobilized support with a biocompatible buffer which preserves the specific binding interaction of the polymeric dye and the specific binding member. Separation and optional washing of unbound material of the sample from the support provides for an enriched population of target cells where undesired cells and material may be removed.

In certain embodiments, the method includes detecting the labeled target analyte. Detecting the labeled target analyte may include exciting the polymeric fluorescent tandem dye with one or more lasers and subsequently detecting fluorescence emission from the polymeric fluorescent tandem dye using one or more optical detectors. Detection of the labeled target can be performed using any convenient instruments and methods, including but not limited to, flow cytometry, FACS systems, fluorescence microscopy; fluorescence, luminescence, ultraviolet, and/or visible light detection using a plate reader; high performance liquid chromatography (HPLC); and mass spectrometry. When using fluorescently labeled components in the methods and compositions of the present disclosure, it is recognized that different types of fluorescence detection systems can be used to practice the subject methods. In some cases, high throughput screening can be performed, e.g., systems that use 96 well or greater microtiter plates. A variety of methods of performing assays on fluorescent materials can be utilized, such as those methods described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In some cases, excitation radiation, from an excitation source having a first wavelength, passes through excitation optics. The excitation optics cause the excitation radiation to excite the sample. In response, fluorescently labelled targets in the sample emit radiation which has a wavelength that is different from the excitation wavelength. Collection optics then collect the emission from the sample. The device can include a temperature controller to maintain the sample at a specific temperature while it is being scanned. In certain instances, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

In some embodiments, the method of evaluating a sample for the presence of a target analyte further includes detecting fluorescence in a flow cytometer. In some embodiments, the method of evaluating a sample for the presence of a target analyte further includes imaging the labelling composition contacted sample using fluorescence microscopy. Fluorescence microscopy imaging can be used to identify a polymeric dye conjugate-target analyte binding complex in the contacted sample to evaluate whether the target analyte is present. Microscopy methods of interest that find use in the subject methods include laser scanning confocal microscopy.

Also provided are methods of producing violet excitable polymeric fluorescent tandem dyes, e.g., as described herein. In some embodiments, the method includes: contacting a specific binding member with a violet excitable polymeric fluorescent tandem dye (e.g., as described herein) to produce a specific binding member/polymeric fluorescent tandem dye conjugate, wherein the polymeric fluorescent tandem dye includes a conjugation tag that covalently links the dye to the specific binding member. The term "conjugation tag" refers to a group that includes a chemo-selective functional group (e.g., as described herein) that can covalently link with a compatible functional group of a specific binding member, after optional activation and/or deprotection. Any convenient conjugation tags may be utilized in the subject polymeric dyes in order to conjugate the polymeric fluorescent tandem dye to specific binding member, e.g., antibody or fragment thereof, of interest. In some embodiments, the conjugation tag includes a terminal functional group selected from an amino, a carboxylic acid or a derivative thereof, a thiol, a hydroxyl, a hydrazine, a hydrazide, an azide, an alkyne and a protein reactive group (e.g., amino-reactive, thiol-reactive, hydroxyl-reactive, imidazolyl-reactive or guanidinyl-reactive). Any convenient methods and reagents may be adapted for use in the subject methods in order to covalently link the conjugation tag to the specific binding member. Methods of interest for labeling a target, include but are not limited to, those methods and reagents described by Hermanson, Bioconjugate Techniques, Third edition, Academic Press, 2013. The contacting step may be performed in an aqueous solution. In some instances, the conjugation tag includes an amino functional group and the target molecule includes an activated ester functional group, such as a NHS ester or sulfo-NHS ester, or vice versa. In certain instances, the conjugation tag includes a maleimide functional group and the target molecule includes a thiol functional group, or vice versa. In certain instances, the conjugation tag includes an alkyne (e.g., a cyclooctyne group) functional group and the target molecule includes an azide functional group, or vice versa, which can be conjugated via Click chemistry. In some cases, the method includes a separating step where the product labeled specific binding member is separated from the reaction mixture, e.g., excess reagents or unlabeled specific binding member. A variety of methods may be utilized to separate a target from a sample, e.g., via immobilization on a support, precipitation, chromatography, and the like.

In some instances, the method further includes detecting and/or analyzing the product labeled specific binding member. In some instances, the method further includes fluorescently detecting the labeled specific binding member. Any convenient methods may be utilized to detect and/or analyze the specific binding member in conjunction with the subject methods and compositions. Methods of analyzing a target of interest that find use in the subject methods, include but are not limited to, flow cytometry, fluorescence microscopy, in-situ hybridization, enzyme-linked immunosorbent assays (ELISAs), western blot analysis, magnetic cell separation assays and fluorochrome purification chromatography. Detection methods of interest include but are not limited to fluorescence spectroscopy, fluorescence microscopy, nucleic acid sequencing, fluorescence in-situ hybridization (FISH), protein mass spectroscopy, flow cytometry, and the like.

Detection may be achieved directly via the polymeric tandem dye, or indirectly by a secondary detection system. The latter may be based on any one or a combination of several different principles including, but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. More than one antibody of specific and/or non-specific nature might be labelled and used simultaneously or sequentially to enhance target detection, identification, and/or analysis.

Systems

Aspects of the invention further include systems for use in practicing the subject methods and compositions. A sample analysis system can include sample field of view or a flow channel loaded with a sample and labeled specific binding member of the invention, e.g., as described above. In some embodiments, the system is a flow Cytometric system including: a flow cytometer including a flow path; a composition in the flow path, wherein the composition includes: a sample and a labeled specific binding member (e.g., as described herein). In some embodiments, the system for analyzing a sample is a fluorescence microscopy system, including: a fluorescence microscope comprising a sample field of view; and a composition disposed in the sample field of view, wherein the composition comprises a sample; and a labelled specific binding member (e.g., as described herein).

In certain embodiments of the systems, the composition further includes a second specific binding member that is support bound and specifically binds the target analyte. In some cases, the support includes a magnetic particle. As such, in certain instances, the system may also include a controllable external paramagnetic field configured for application to an assay region of the flow channel.

The sample may include a cell. In some instances, the sample is a cell-containing biological sample. In some instances, the sample includes a labelled specific binding member specifically bound to a target cell. In certain instances, the target analyte that is specifically bound by the specific binding member is a cell surface marker of the cell. In certain cases, the cell surface marker is selected from a cell receptor and a cell surface antigen.

In certain aspects, the system may also include a light source configured to direct light to an assay region of the flow channel or sample field of view. The system may include a detector configured to receive a signal from an assay region of the flow channel or a sample field of view, wherein the signal is provided by the fluorescent composition. Optionally further, the sample analysis system may include one or more additional detectors and/or light sources for the detection of one or more additional signals.

In certain aspects, the system may further include computer-based systems configured to detect the presence of the fluorescent signal. A "computer-based system" refers to the hardware means, software means, and data storage means used to analyze the information of the present invention. The minimum hardware of the computer-based systems of the present invention includes a central processing unit (CPU), input means, output means, and data storage means. A skilled artisan can readily appreciate that any one of the currently available computer-based system are suitable for use in the subject systems. The data storage means may include any manufacture including a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g., word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

In addition to the sensor device and signal processing module, e.g., as described above, systems of the invention may include a number of additional components, such as data output devices, e.g., monitors and/or speakers, data input devices, e.g., interface ports, keyboards, etc., fluid handling components, power sources, etc.

In certain aspects, the system includes a flow cytometer. Suitable flow cytometry systems may include, but are not limited to, those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry,* 3rd ed., Wiley-Liss (1995); Virgo, et al. (2012) *Ann Clin Biochem*. January;49(pt 1):17-28; Linden, et. al., *Semin Throm Hemost*. 2004 October; 30(5):502-11; Alison, et al. *J Pathol,* 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ flow cytometer, BD Biosciences FACSCanto™ II flow cytometer, BD Accurim™ flow cytometer, BD Accuri™ C6 Plus flow cytometer, BD Biosciences FACSCelesta™ flow cytometer, BD Biosciences FACSLyric™ flow cytometer, BD Biosciences FACSVerse™ flow cytometer, BD Biosciences FACSymphony™ flow cytometer, BD Biosciences LSRFortessa™ flow cytometer, BD Biosciences LSR-Fortessa™ X-20 flow cytometer, BD Biosciences FACSPresto™ flow cytometer, BD Biosciences FACSVia™ flow cytometer and BD Biosciences FACSCalibur™ cell sorter, a BD Biosciences FACSCount™ cell sorter, BD Biosciences FACSLyric™ cell sorter, BD Biosciences Via™ cell sorter, BD Biosciences Influx™ cell sorter, BD Biosciences Jazz™ cell sorter, BD Biosciences Aria™ cell sorter, BD Biosciences FACSAria™ II cell sorter, BD Biosciences FACSAria™ III cell sorter, BD Biosciences FACSAria™ Fusion cell sorter and BD Biosciences FACSMelody™ cell sorter, BD Biosciences FACSymphony™ S6 cell sorter or the like.

In some embodiments, the subject systems are flow Cytometric systems, such those described in U.S. Pat. Nos. 10,663,476; 10,620,111; 10,613,017; 10,605,713; 10,585,031; 10,578,542; 10,578,469; 10,481,074; 10,302,545; 10,145,793; 10,113,967; 10,006,852; 9,952,076; 9,933,341; 9,726,527; 9,453,789; 9,200,334; 9,097,640; 9,095,494; 9,092,034; 8,975,595; 8,753,573; 8,233,146; 8,140,300; 7,544,326; 7,201,875; 7,129,505; 6,821,740; 6,813,017; 6,809,804; 6,372,506; 5,700,692; 5,643,796; 5,627,040; 5,620,842; 5,602,039; 4,987,086; 4,498,766; the disclosures of which are herein incorporated by reference in their entirety.

In certain instances, flow cytometry systems of the invention are configured for imaging particles in a flow stream by fluorescence imaging using radiofrequency tagged emission (FIRE), such as those described in Diebold, et al. Nature Photonics Vol. 7(10); 806-810 (2013) as well as described in U.S. Pat. Nos. 9,423,353; 9,784,661; 9,983,132; 10,006,852; 10,078,045; 10,036,699; 10,222,316; 10,288,546; 10,324,019; 10,408,758; 10,451,538; 10,620,111; and U.S. Patent Publication Nos. 2017/0133857; 2017/0328826; 2017/0350803; 2018/0275042; 2019/0376895 and 2019/0376894 the disclosures of which are herein incorporated by reference.

Other systems may find use in practicing the subject methods. In certain aspects, the system may be a fluorimeter or microscope loaded with a sample having a fluorescent composition of any of the embodiments discussed herein. The fluorimeter or microscope may include a light source configured to direct light to the assay region of the flow channel or sample field of view. The fluorimeter or microscope may also include a detector configured to receive a signal from an assay region of the flow channel or field of view, wherein the signal is provided by the fluorescent composition.

Kits

Aspects of the invention further include kits for use in practicing the subject methods and compositions. The compositions of the invention can be included as reagents in kits either as starting materials or provided for use in, for example, the methodologies described above. A kit can include a labeled specific binding member, e.g., as described above, and a container. Any convenient containers can be utilized, such as tubes, bottles, or wells in a multi-well strip or plate, a box, a bag, an insulated container, and the like. The subject kits can further include one or more components selected from a primer specific binding member for a given target analyte, a support bound specific binding member, a cell, a support, a biocompatible aqueous elution buffer, a control (positive and/or negative), etc., and instructions for use, as desired. A given kit may include reagents suitable for a detection of a single target analyte, or multiple reangest suitable for detection of two or more different target analytes, e.g., where a given kit is configured for multiplex detection applications.

In certain embodiments, the kit finds use in evaluating a sample for the presence of a target analyte, such as an intracellular target. As such, in some instances, the kit includes one or more components suitable for permeabilizing or lysing cells. The one or more additional components of the kit may be provided in separate containers (e.g., separate tubes, bottles, or wells in a multi-well strip or plate).

In certain aspects, the kit further includes reagents for performing a flow cytometric assay. Reagents of interest include, but are not limited to, buffers for reconstitution and dilution, buffers for contacting a cell sample the chromophore, wash buffers, control cells, control beads, fluorescent beads for flow cytometer calibration and combinations thereof. The kit may also include one or more cell fixing reagents such as paraformaldehyde, glutarakiehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The compositions of the kit may be provided in a liquid composition, such as any suitable buffer. Alternatively, the compositions of the kit may be provided in a dry composition (e.g., may be lyophilized), and the kit may optionally include one or more buffers for reconstituting the dry composition. In certain aspects, the kit may include aliquots of the compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The violet excitable tandem dyes and labeled specific binding members comprising the same, compositions, methods and systems as described herein may find use in a variety of applications, including diagnostic and research applications, in which the labelling, detection and/or analysis of a target of interest is desirable. Such applications include methodologies such as cytometry, microscopy, immunoassays (e.g. competitive or non-competitive), assessment of a free analyte, assessment of receptor bound ligand, and so forth. The compositions, system and methods described herein may be useful in analysis of any of a number of samples, including but not limited to, biological fluids, cell culture samples, and tissue samples. In certain aspects, the compositions, system and methods described herein may find use in methods where analytes are detected in a sample, if present, using fluorescent labels, such as in fluorescent activated cell sorting or analysis, immunoassays, immunostaining, and the like. In certain instances, the compositions and methods find use in applications where the evaluation of a sample for the presence of a target analyte is of interest.

In some cases, the methods and compositions find use in any assay format where the detection and/or analysis of a target from a sample is of interest, including but not limited to, flow cytometry, fluorescence microscopy, in-situ hybridization, enzyme-linked immunosorbent assays (ELISAs), western blot analysis, magnetic cell separation assays and fluorochrome purification chromatography. In certain instances, the methods and compositions find use in any application where the fluorescent labelling of a target molecule is of interest. The subject compositions may be adapted for use in any convenient applications where pairs of specific binding members find use, such as biotin-streptavidin and hapten-anti-hapten antibody.

The following examples are offered by way of illustration and not by way of limitation.

EXAMPLES

I. Synthesis of Water-Soluble Violet Excitable Coumarin Donor Fluorophores C, G and H

A. Synthesis of Compound C

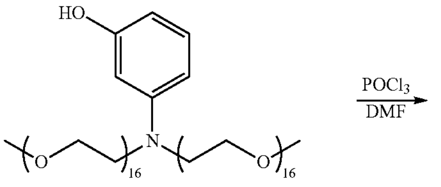

-continued

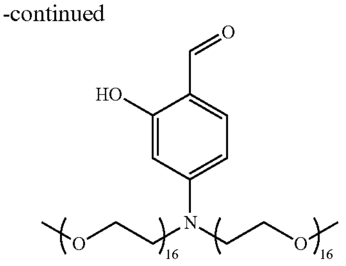

1C

Compound 1C: The reaction A of $POCl_3$ (40.82 mg, 266.23 umol, 24.74 uL, 0.1 eq) in DMF (45 mL) at 0° C. for 0.5 hr under $N_2$ atmosphere, the mixture B of 3-[bis[2-[2-[2-[2-[2-[2-[2-[2-[2-[2-[2-(2-methoxyethoxy) ethoxy]ethoxy]ethoxy]ethoxy]ethoxy]ethoxy]ethoxy]ethoxy]ethoxy]ethoxy]ethyl]amino]phenol (3.18 g, 2.66 mmol, 1 eq) in DMF (40 mL), the mixture were added to the stirred solution. The resulting mixture was stirred at 25° C. for 16 hours. The reaction mixture was acidified with $Na_2CO_3$ to pH=7, the mixture was stirred at 55° C. for 3 hr under $N_2$ atmosphere. The mixture was extracted with DCM (200 mL) and $H_2O$ (100 mL), the combined organic phases were washed with brine (100 mL), dried with anhydrous $Na_2SO_4$, concentrated to obtain crude residue. The residue was used for next step without purification. Compound 4-[bis[2-[2-[2-[2-[2-[2-[2-[2-[2-[2-[2-(2-methoxyethoxy)ethoxy]ethoxy]ethoxy]ethoxy]ethoxy]ethoxy]ethoxy]ethoxy]ethoxy]ethoxy]ethyl]amino]-2-hydroxy-benzaldehyde (Compound 1C) (1.83 g, 1.18 mmol, 44.31% yield, 78.8% purity) was obtained as a light black oil.

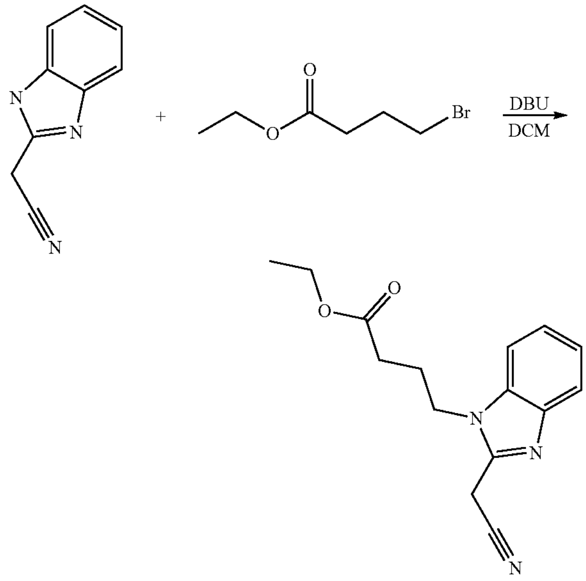

2C

Compound 2C: To a solution of 2-(1H-benzimidazol-2-yl) acetonitrile (2 g, 12.72 mmol, 1 eq) in DCM (100 mL) was added DBU (2.32 g, 15.27 mmol, 2.30 mL, 1.2 eq) and ethyl 4-bromobutanoate (3.72 g, 19.09 mmol, 2.74 mL, 1.5 eq). The mixture was stirred at 50° C. under $N_2$ for 16 hr. The mixture was concentrated under reduced pressure to obtain a residue. The residue was purified by flash silica gel chromatography. Ethyl 4-[2-(cyanomethyl) benzimidazol-1-yl]butanoate (Compound 2C) (1.33 g, 4.52 mmol, 35.52% yield, 92.2% purity) was obtained as a dark black oil.

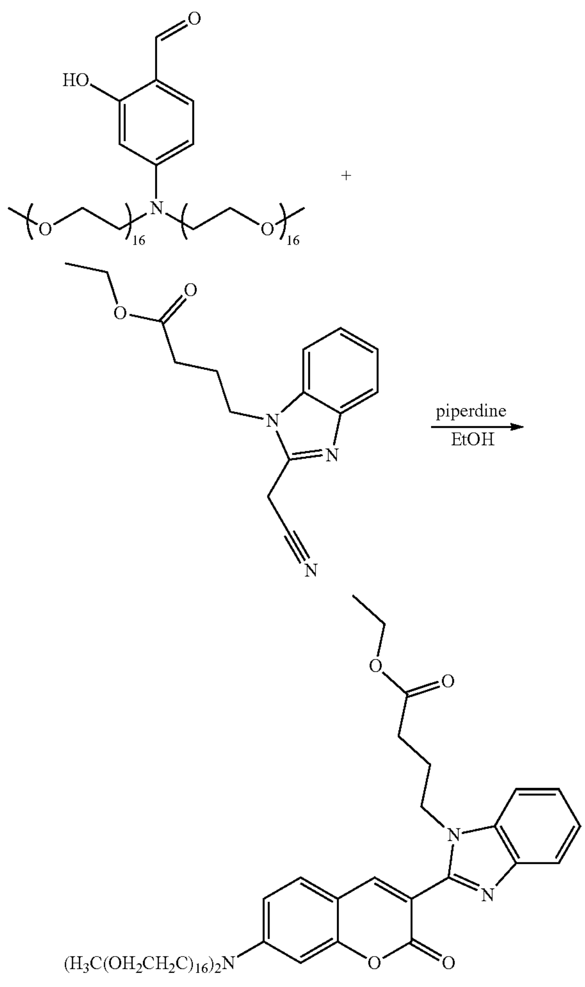

3C

Compound 3C: To a solution of Compound 1C (0.2 g, 163.61 umol, 1 eq) and Compound 2C (66.58 mg, 245.41 umol, 1.5 eq) in EtOH (4 mL) was added piperdine (27.86 mg, 327.21 umol, 32.31 uL, 2 eq) under $N_2$ atmosphere. Some yellow solid was precipitated from the mixture. The suspension was stirred at 55° C. for 16 hr. The mixture was dissolved in DCM (50 mL), washed with water (20 mL) and brine (10 mL), the organic layer was dried dover $Na_2SO_4$, filtered and concentrated under reduced pressure to obtain a residue. The crude product was stirred in 2% HCl (2 mL) at 100° C. for 2 hr under $N_2$ atmosphere. The mixture was cooled in room temperature then dissolved in DCM (100 mL), washed with water (10 mL) and brine (10 mL), the organic layer was dried dover $Na_2SO_4$, filtered and concentrated under reduced pressure to obtain a residue. Ethyl 4-[2-[7-[bis[2-[2-[2-[2-[2-[2-[2-[2-[2-[2-[2-(2-methoxy-ethoxy) ethoxy]ethoxy]ethoxy]ethoxy]ethoxy]ethoxy] ethoxy]ethoxy]ethoxy]ethoxy]ethyl]amino]-2-oxo-chromen-3-yl]benzimidazol-1-yl]butanoate (Compound 3C) (0.25 g, 155.75 umol, 95.20% yield, 92% purity) was obtained as a yellow oil.

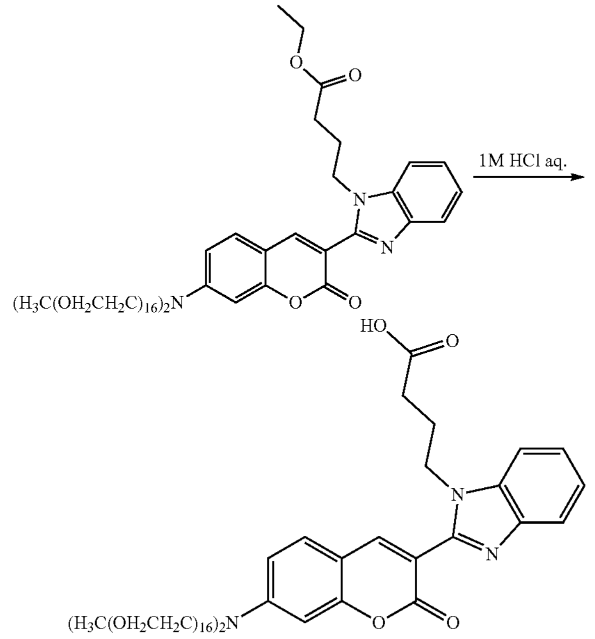

C

Compound C: To a solution of Compound 3C (0.05 g, 33.86 umol, 1 eq) in HCl (2.04 g, 5.60 mmol, 2 mL, 10% purity, 165.25 eq) at 100° C. for 1 hr under $N_2$ atmosphere. The mixture was dissolved in DCM (50 mL), the organic layer was dried dover $Na_2SO_4$, filtered and concentrated under reduced pressure to obtain a residue. The resulting residue was purified by prep-HPLC. Compound 4-[2-[7-[bis[2-[2-[2-[2-[2-[2-[2-[2-[2-[2-[2-(2-methoxyethoxy) ethoxy] ethoxy]ethoxy]ethoxy]ethoxy]ethoxy]ethoxy]ethoxy] ethoxy]ethoxy]ethyl]amino]-2-oxo-chromen-3-yl] benzimidazol-1-yl]butanoic acid (Compound C) (0.75 g, 509.95 umol, 56.83% yield, 98.5% purity) was obtained as a yellow oil.

B. Synthesis of Compound G

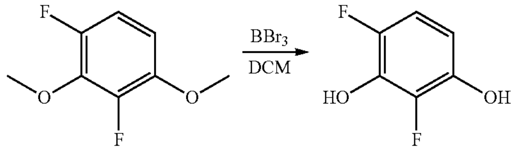

1G

Compound 1G: 1,3-difluoro-2,4-dimethoxy-benzene (3 g, 17.23 mmol, 1 eq) was diluted in DCM (114 mL) and a $BBr_3$ (1 M, 111.11 mL, 6.45 eq) was added to via cannula at 20° C. The resulting clear light brown solution was stirred 40 hr at 20° C. The reaction was quenched by a slow addition to a suspension of ice in $H_2O$ (400 mL), causing formation of a precipitate. The resulting suspension was stirred at r.t. until the precipitate dissolved. The organic layer was decanted, and the aqueous layers from both reactions were combined and extracted until it was nearly colorless using $CH_2Cl_2$ (3×50 mL). The $CH_2Cl_2$ layer was discarded and the aqueous layer was extracted with MTBE (3×300 mL). The combined ether layers were dried ($MgSO_4$), filtered, and concentrated under reduced pressure to give a light gray semi-solid. Crystallization was induced by retaking the solids in portions of $CH_2Cl_2$ until a precipitate formed (10 mL), followed by solvent removal under reduced pressure until a free flowing light gray powder was obtained. 2,4-difluorobenzene-1,3-diol (Compound 1G)(2.5 g, 15.40 mmol, 89.40% yield, 90% purity) was obtained as a light gray solid.

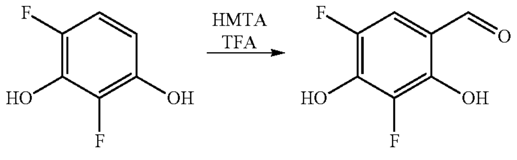

2G

Compound 2G: TFA (46.15 g, 404.71 mmol, 29.97 mL, 23.65 eq) was charged into a 100 mL flask and cooled to 0° C. HMTA (4.80 g, 34.23 mmol, 6.40 mL, 2 eq) was slowly added to the cold TFA with stirring at a rate that maintained the reaction temperature around 0° C. Compound 1G (2.5 g, 17.11 mmol, 1 eq) was then added as a solid in one portion. The flask was equipped with a reflux condenser and was flushed with $N_2$ around 90° C. The reaction mixture was refluxed for 24 h during which the solution slowly turned brown. The mixture was allowed to cool to r.t. The reaction was quenched at r.t. with 20% aq H2SO4 (14 mL) and stirred at r.t. for an additional 4 h. The mixture was poured into ice H2O (100 mL) and extracted with EtOAc (3×50 mL). The combined organic layers were washed with brine (1×100 mL), then directly concentrated under reduced pressure to obtain a thick orange semisolid. The residue was purified by flash silica gel chromatography 3,5-difluoro-2,4-dihydroxy-benzaldehyde (Compound 2G) (1.26 g, 7.13 mmol, 41.69% yield, 98.57% purity) was obtained as a yellow solid.

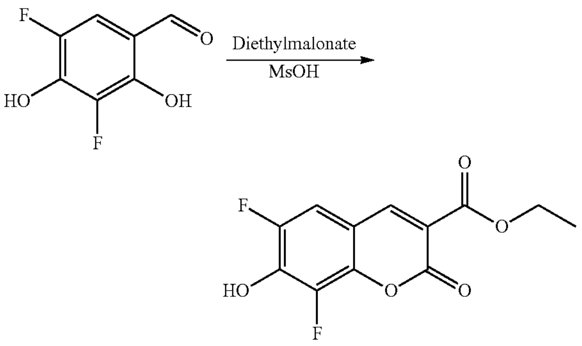

3G

Compound 3G: Compound 2G (1.26 g, 7.24 mmol, 1 eq) and diethyl malonate (4.50 g, 28.08 mmol, 4.24 mL, 3.88 eq) were charged into a flask, followed by addition of MsOH (89.5 mL) at 20° C. with vigorous stirring. The reaction mixture was immediately protected from light with foil and flushed with $N_2$. The mixture was stirred for 16 h. The mixture was worked up by pouring it onto ice water (50 mL) and extraction with EtOAc (3×50 mL). The combined organic layers were washed with H2O (3×50 mL) and brine (1×50 mL). The organic layer was dried ($Na_2SO_4$), filtered, and concentrated under reduced pressure. The residue was redissolved with MeCN (6.5 mL) in a flask, flushed with $N_2$, and then heated until all the solids had dissolved. The solution was allowed to cool slowly to r.t. followed by further cooling at 4° C. for 1 h. Yellow crystals formed, which were collected by vacuum filtration and washed with MTBE (3×4.5 mL). The product was a fluffy yellow powder. Ethyl 6,8-difluoro-7-hydroxy-2-oxo-chromene-3-carboxylate (Compound 3G) (1.2 g, 4.31 mmol, 59.54% yield, 97.02% purity) was obtained as a light yellow solid.

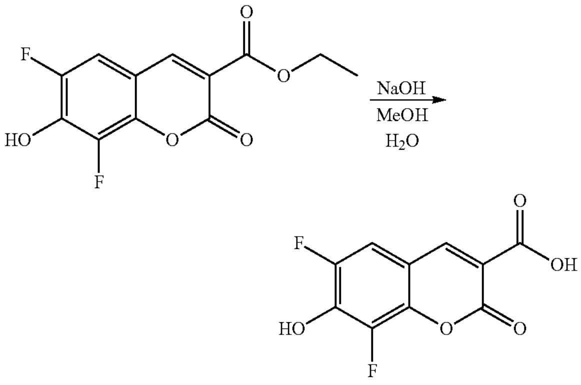

4G

Compound 4G: In a flask was dissolved NaOH (799.39 mg, 19.99 mmol, 54 eq) in H2O (10 mL) MeOH (2 mL) was added to the flask, followed by Compound 3G (0.1 g, 370.12 umol, 1 eq). The reaction mixture was immediately protected from light and stirred at 20° C. for 1 hr.

The reaction solution was acidified with concentrated HCl (50 mL) causing it to become nearly colorless and was extracted with EtOAc (3×100 mL). The combined organic layers were washed with brine (1×50 mL), dried (MgSO4), filtered, and concentrated under reduced pressure and protected from light. 6,8-difluoro-7-hydroxy-2-oxo-chromene-3-carboxylic acid (Compound 4G) (70 mg, 287.45 umol, 77.66% yield, 99.43% purity) was obtained as a light yellow solid.

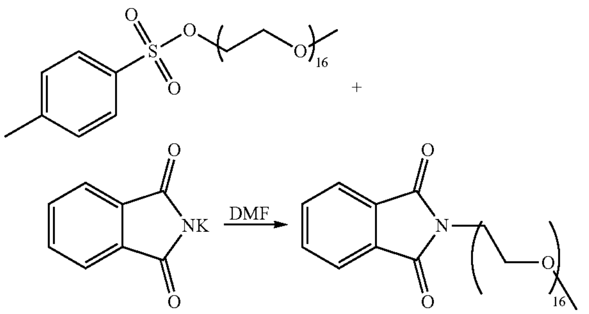

5G

Compound 5G: To a solution of 2-[2-[2-[2-[2-[2-[2-[2-[2-[2-[2-[2-[2-[2-[2-(2-methoxyethoxy) ethoxy]ethoxy] ethoxy]ethoxy]ethoxy]ethoxy]ethoxy]ethoxy]ethoxy] ethoxy]ethoxy]ethoxy]ethoxy]ethoxy]ethyl 4-methylbenzenesulfonate (20 g, 22.45 mmol, 1 eq) in DMF (240 mL) was added (1,3-dioxoisoindolin-2-yl) potassium (4.99 g, 26.93 mmol, 1.2 eq). Then the reaction mixture was stirred at 100° C. for 12 hr under nitrogen to afford a colorless solution. The reaction mixture was extracted with DCM (100 mL×3) and water (200 mL), the organic layer was washed with water (200 mL×3). The separated organic layer was dried over Na2SO4, filtered and evaporated to afford a residue. Compound 2-[2-[2-[2-[2-[2-[2-[2-[2-[2-[2-[2-[2-[2-[2-[2-(2-methoxyethoxy) ethoxy]ethoxy]ethoxy]ethoxy]ethoxy]ethoxy]ethoxy]ethoxy]ethoxy]ethoxy]ethoxy]ethoxy]ethoxy]ethoxy]ethyl]isoindoline-1,3-dione (Compound 5G) (8 g, 8.82 mmol, 39.28% yield, 95.43% purity) was obtained as a light yellow oil.

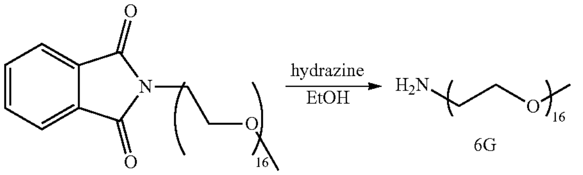

6G

Compound 6G: To a mixture of solid Compound 5G (8 g, 9.24 mmol, 1 eq) and EtOH (160 mL) was added hydrazine; hydrate (1.76 g, 35.10 mmol, 1.71 mL, 3.8 eq) in one charge. It was heated to 40° C. for 4 hr. The reaction mixture was cooled to 20° C., then filtered, the filter cake was washed with DCM (100 mL×2), the filter was evaporated to afford a residue, the residue was dissolved in DCM (50 mL) and filtered, the filter cake was washed with DCM (50 mL×2), the filter was evaporated to afford the desired product. The residue was directly used for next step and no further purified. Compound 2-[2-[2-[2-[2-[2-[2-[2-[2-[2-[2-[2-[2-[2-[2-(2-methoxyethoxy) ethoxy]ethoxy]ethoxy]ethoxy]ethoxy]ethoxy]ethoxy]ethoxy]ethoxy]ethoxy]ethoxy]ethoxy]ethoxy]ethoxy]ethanamine (Compound 6G) (6.6 g, crude) was obtained as a light yellow oil.

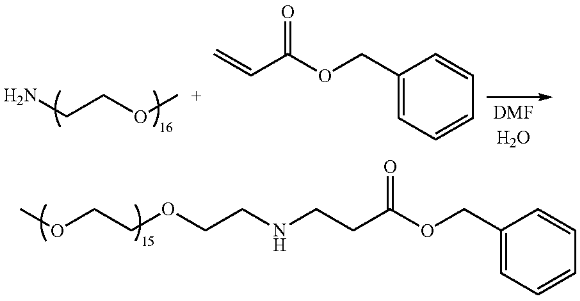

7G

Compound 7G: To a solution of Compound 6G (5 g, 6.79 mmol, 1 eq) in DMF (20 mL) and $H_2O$ (15 mL) was added benzyl prop-2-enoate (1.10 g, 6.79 mmol, 1 eq). Then the reaction mixture was stirred at 20° C. for 16 hr under nitrogen to afford a colorless solution. The reaction mixture was cooled to 20° C., then filtered, the filter cake was washed with DCM (20 mL×2), the filter was evaporated to afford a residue, the residue was dissolved in DCM (30 mL) and filtered, the filter cake was washed with DCM (20 mL×2), the filter was evaporated to afford the desired product. The crude product was purified by reversed-phase HPLC (0.075% TFA condition) to give the product 3 g. The 3 g residue was purified by prep-HPLC. Compound benzyl 3-[2-[2-[2-[2-[2-[2-[2-[2-[2-[2-[2-[2-[2-[2-[2-(2-methoxy-ethoxy) ethoxy]ethoxy]ethoxy]ethoxy]ethoxy]ethoxy]ethoxy]ethoxy]ethoxy]ethoxy]ethoxy]ethoxy]ethoxy]ethoxy]ethylamino]propanoate (Compound 7G) (2 g, 2.00 mmol, 29.50% yield, 90% purity) was obtained as a colorless oil.

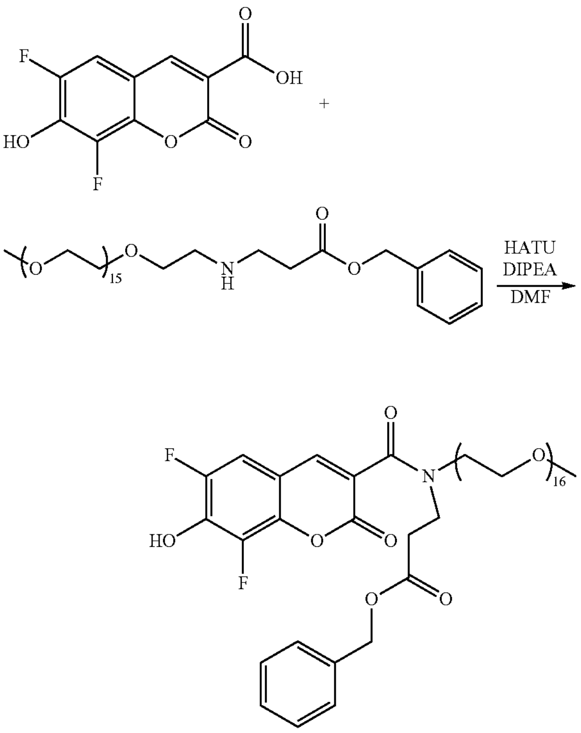

8G

Compound 8G: To a solution of Compound 4G (50 mg, 206.50 umol, 1 eq) in DMF (2 mL) was added HATU (102.07 mg, 268.45 umol, 1.3 eq) and DIEA (106.75 mg, 825.99 umol, 143.87 uL, 4 eq). The reaction mixture was stirred at 20° C. for 0.5 hr under nitrogen. Then Compound 7G (222.54 mg, 247.80 umol, 1.2 eq) was added to the above solution and stirred at 20° C. for 2 hr under nitrogen to obtain a green solution. The reaction mixture was poured into water (10 mL) and extracted with DCM (20 mL×3), the combined organic phases were washed with water (20 mL) and saturated NaCl (20 mL), then dried over anhydrous Na2SO4, concentrated to obtain a green residue. The residue was directly used for next step and no further purified. Compound benzyl 3-[(6,8-difluoro-7-hydroxy-2-oxo-chromene-3-carbonyl)-[2-[2-[2-[2-[2-[2-[2-[2-[2-[2-[2-[2-[2-[2-[2-(2-methoxyethoxy) ethoxy]ethoxy]ethoxy]ethoxy]ethoxy]ethoxy]ethoxy]ethoxy]ethoxy]ethoxy]ethoxy]ethoxy]ethoxy]ethoxy]ethyl]amino]propanoate (Compound 8G) (200 mg, crude) was obtained as a light yellow oil.

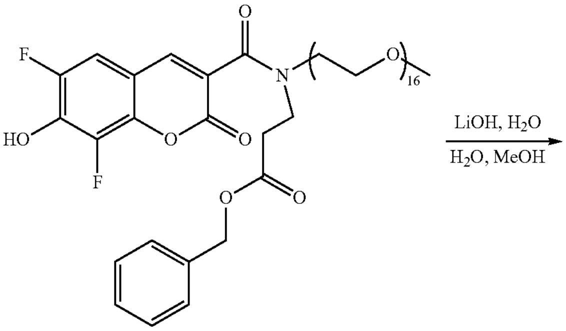

-continued

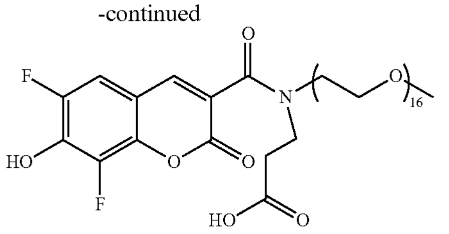

G

Compound G: In a flask was dissolved LiOH·H2O (6.42 mg, 152.94 umol, 2 eq) in MeOH (1 mL), H2O (0.2 mL) was added to the flask, followed by Compound 8G (0.08 g, 76.47 umol, 1 eq). The reaction mixture was immediately protected from light and stirred at 20° C. for 1 hr. The reaction solution was acidified with concentrated HCl (5 mL) causing it to become nearly colorless and was extracted with EtOAc (3×100 mL). The combined organic layers were washed with brine (1×50 mL), dried (MgSO4), filtered, and concentrated under reduced pressure and protected from light. The residue was purified by prep-HPLC (column: Boston Green ODS 150*30 mm*5 um; mobile phase: [water (0.075% TFA)-ACN]; B %: 15%-45%, 9 min). Compound 3-[(6,8-difluoro-7-hydroxy-2-oxo-chromene-3-carbonyl)-[2-[2-[2-[2-[2-[2-[2-[2-[2-[2-[2-[2-[2-[2-[2-(2-methoxyethoxy) ethoxy]ethoxy]ethoxy]ethoxy]ethoxy]ethoxy]ethoxy] ethoxy]ethoxy]ethoxy]ethoxy]ethoxy]ethoxy]ethoxy]ethyl] amino]propanoic acid (Compound G) (40 mg, 38.72 umol, 50.63% yield, 99.9% purity) was obtained as a colorless oil.

C. Synthesis of Compound H

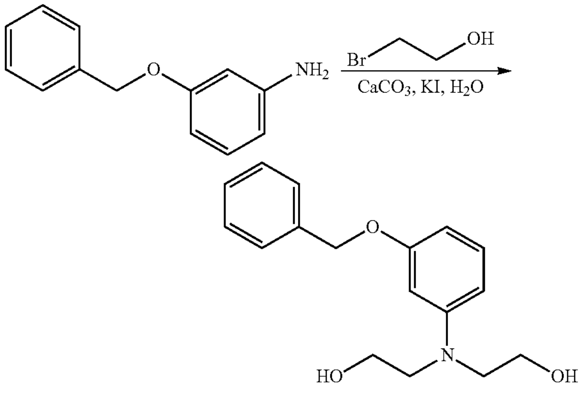

1H

Compound 1H: A mixture of 3-benzyloxyaniline (20 g, 100.38 mmol, 1 eq), 2-bromoethanol (50.17 g, 401.51 mmol, 28.51 mL, 4 eq), $CaCO_3$ (20.09 g, 200.75 mmol, 2 eq), KI (1.67 g, 10.04 mmol, 0.1 eq) in $H_2O$ (200 mL) The mixture was stirred at 100° C. for 16 hr. The mixture was extracted with ethyl acetate (3×200 mL), the combined organic layers were washed with brine (100 mL), dried over $Na_2SO_4$, filtered and concentrated under reduced pressure. The residue was purified by column chromatography ($SiO_2$, Petroleum ether:Ethyl acetate=1:1). Compound 2-[3-benzyloxy-N-(2-hydroxyethyl) anilino]ethanol (30 g, 89.79 mmol, 89.45% yield, 86% purity) was obtained as a yellow oil.

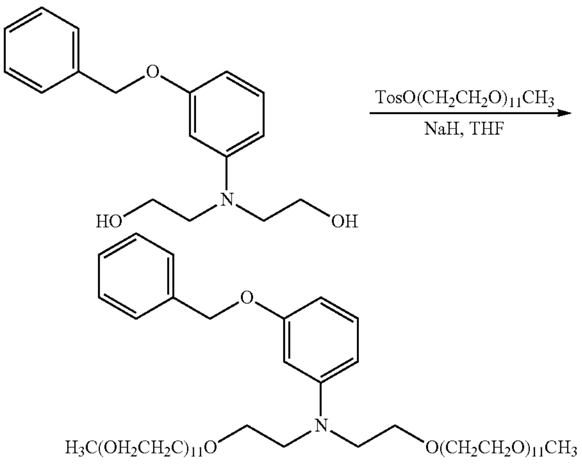

2H

Compound 2H: To a solution of Compound 1H (4 g, 13.92 mmol, 1 eq) in THF (320 mL) was added NaH (5.57 g, 139.20 mmol, 60% purity, 10 eq) under $N_2$ atmosphere. The mixture was stirred at 70° C. for 1 hr. Then the mixture was cooled to 25° C., a solution of 2-[2-[2-[2-[2-[2-[2-[2-[2-[2-(2-methoxyethoxy) ethoxy]ethoxy]ethoxy]ethoxy]ethoxy] ethoxy]ethoxy]ethoxy]ethoxy]ethyl 4-methylbenzenesulfonate (22.41 g, 33.41 mmol, 2.4 eq) was added drop wise. The mixture was stirred at 70° C. for another 16 hr. The mixture was quenched with water (200 mL), extracted with $CH_2Cl_2$ (600 mL), the combined organic layers were washed with brine (200 mL), dried over $Na_2SO_4$, filtered and concentrated under reduced pressure. The residue was purified by column chromatography ($SiO_2$, Dichloromethane: Methanol=10:1). Compound 2H, 3-benzyloxy-N, N-bis[2-[2-[2-[2-[2-[2-[2-[2-[2-[2-[2-(2-methoxyethoxy) ethoxy] ethoxy]ethoxy]ethoxy]ethoxy]ethoxy]ethoxy]ethoxy] ethoxy]ethoxy]ethyl]aniline (22 g, 13.87 mmol, 99.66% yield, 81% purity) was obtained as a yellow oil, which was checked by LCMS and HPLC.

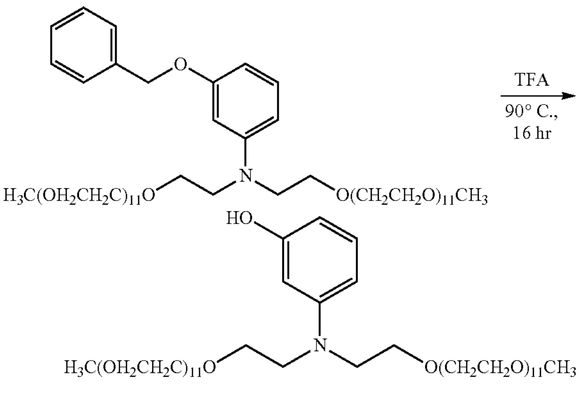

3H

Compound 3H: To a solution of Compound 2H (22 g, 17.13 mmol, 1 eq) added in TFA (200 mL), the mixture was stirred at 90° C. for 16 hr. The reaction mixture was acidified with $NaHCO_3$ to pH=7, filtered and the cake was washed with H2O (200 mL) and DCM (400 mL), then concentrated under reduced pressure to give a residue. The residue was purified by column chromatography ($SiO_2$, Dichloromethane:Methanol=10:1).

Compound 3-[bis[2-[2-[2-[2-[2-[2-[2-[2-[2-[2-[2-(2-methoxyethoxy) ethoxy]ethoxy]ethoxy]ethoxy]ethoxy] ethoxy]ethoxy]ethoxy]ethoxy]ethoxy]ethyl]amino]phenol (Compound 3H) (13 g, 8.49 mmol, 49.57% yield, 78% purity) was obtained as a black brown oil, which was checked by LCMS and HPLC.

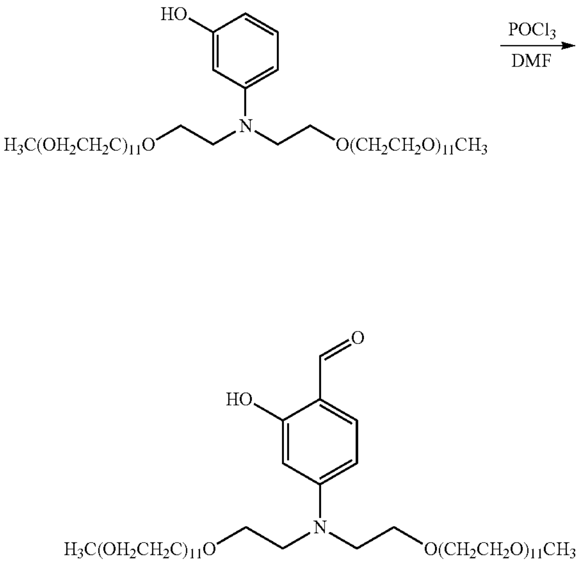

4H

Compound 4H: $POCl_3$ (1.67 g, 10.88 mmol, 1.01 mL, 1 eq) in DMF (130 mL) is stirred at 0° C. for 0.5 hr under $N_2$ atmosphere. Compound 3H (13 g, 10.88 mmol, 1 eq) in DMF (96 mL) was added to the stirred solution. The resulting mixture was stirred at 25° C. for 16 hr. The reaction mixture was acidified with Na2CO3 to pH=7, the mixture was stirred at 55° C. for 3 hr under $N_2$ atmosphere. The mixture was extracted with DCM (500 mL) and $H_2O$ (300 mL), the combined organic phases were washed with brine (300 mL), dried with anhydrous $Na_2SO_4$, concentrated to obtain crude residue. Compound 4-[bis[2-[2-[2-[2-[2-[2-[2-[2-[2-[2-[2-(2-methoxyethoxy) ethoxy]ethoxy]ethoxy] ethoxy]ethoxy]ethoxy]ethoxy]ethoxy]ethoxy]ethoxy]ethyl] amino]-2-hydroxy-benzaldehyde (Compound 4H) (11.5 g, crude) was obtained as a black brown oil, which was checked by LCMS and HPLC, and HNMR.

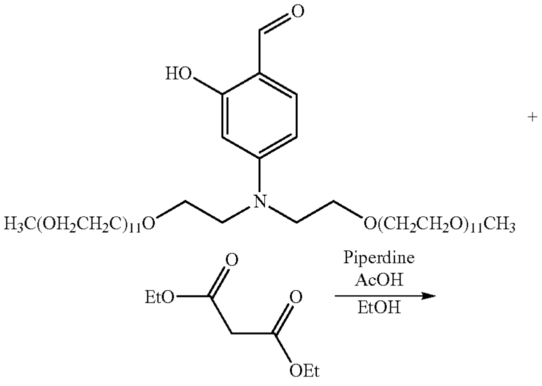

-continued

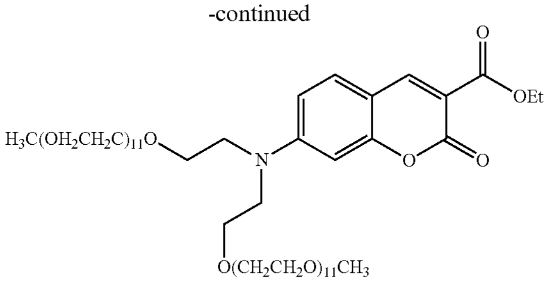

5H

Compound 5H: To a solution of Compound 4H (2 g, 1.64 mmol, 1 eq) and diethyl propanedioate (786.13 mg, 4.91 mmol, 741.63 uL, 3 eq) in EtOH (10 mL) was added piperdine (278.62 mg, 3.27 mmol, 323.15 uL, 2 eq) and AcOH (314.99 mg, 5.25 mmol, 299.99 uL, 3.21 eq). The mixture was stirred at 55° C. for 16 hr. The mixture was quenched with water (100 mL), extracted with $CH_2Cl_2$ (150 mL), the combined organic layers were washed with brine (50 mL), dried over $Na_2SO_4$, filtered and concentrated under reduced pressure The residue was purified by column chromatography (SiO2, Dichloromethane:Methanol=10:1). The residue was purified by prep-HPLC (column: Welch Xtimate C18 150*30 mm*5 um; mobile phase: [water(FA)-ACN]; B %: 20%-50%, 7.7 min). Ethyl 7-[bis[2-[2-[2-[2-[2-[2-[2-[2-[2-[2-[2-(2-methoxyethoxy)ethoxy]ethoxy]ethoxy]ethoxy] ethoxy]ethoxy]ethoxy]ethoxy]ethoxy]ethoxy]ethyl]amino]-2-oxo-chromene-3-carboxylate (Compound 5H) (350 mg, 260.14 umol, 26.38% yield, 98% purity) was obtained as a yellow oil, which was checked by LCMS and HPLC.

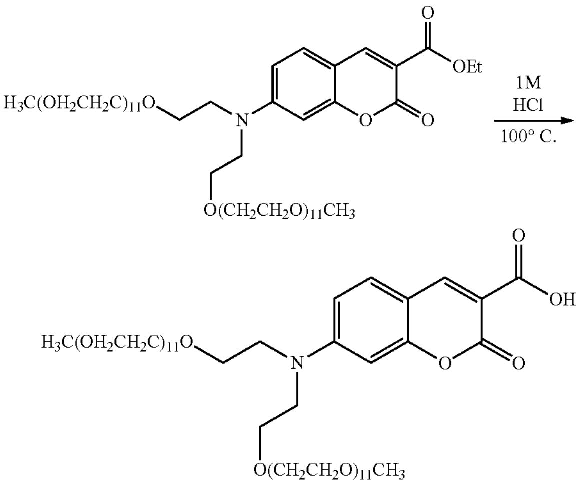

H

Compound H: Compound 5H (300 mg, 227.53 umol, 1 eq) was stirred in 1M HCl (1 M, 227.53 uL, 1 eq) at 100° C. for 1 hr. The mixture was dissolved in DCM (50 mL), the organic layer was dried dover $Na_2SO_4$, filtered and concentrated under reduced pressure to obtain a residue. The residue was purified by reversed phase column (column: 12 g C18 reversed phase column; mobile phase: [Water-ACN]; B %: 0%-60%, 30 min). Compound 7-[bis[2-[2-[2-[2-[2-[2-[2-[2-[2-[2-[2-(2-methoxyethoxy) ethoxy]ethoxy]ethoxy] ethoxy]ethoxy] ethoxy]ethoxy]ethoxy]ethoxy]ethoxy]ethyl] amino]-2-oxo-chromene-3-carboxylic acid (Compound H)

(73.3 mg, 55.10 umol, 24.22% yield, 97% purity) was obtained as a brown oil, which was checked by LCMS and HPLC and 1H NMR.

II. Characterization of Compounds C, G and H

A. UV-Vis Spectroscopy

A UV-2600 Spectrophotometer (double beam, single monochromator Shimadzu Scientific Instruments) was set to collect data for 1 nm increments at a slit width of 1.0 nm from 900 nm to 250 nm. A stock solution of Donor C dissolved in 1× phosphate buffered saline (PBS) was prepared, and 2 mL was transferred to a sample cuvette [1-cm polymethylmethacrylate cuvette]. Then 2 mL of 1×PBS was transferred to a second cuvette. The cuvette containing 1×PBS was placed in the blank cuvette position inside the UV-2600, while the dye sample cuvette was placed in the sample cuvette position. The instrument absorbance was auto-zeroed at 900 nm, and the UV-Vis spectrum was collected from 900 nm to 250 nm. The same protocol was performed with Donors G and H.

B. Fluorescence Spectroscopy

A small volume of Donor C stock solution in 1×PBS was diluted to 25 mA.U. in a total volume of 2 mL 1×PBS. This solution was transferred to a sample cuvette [1-cm polymethylmethacrylate cuvette] and placed inside the sample compartment of a fluorometer. The excitation wavelength was set to 375 nm, and the emission scan range was set to 400 nm to 900 nm. For signal detection, fluorescence signal (S1) and instrument noise (R1) were both recorded. A correction file applied to the raw output signals transformed the S1 and R1 signals to corrected fluorescence (S1c) and corrected noise (R1c). The corrected fluorescence S1c was then normalized with respect to the corrected noise to give the final reported fluorescence emission of the sample. The same protocol was performed with Donors G and H. Results are provided in FIG. 1.

III. Synthesis of Tandem Dyes Having Violet Excitable Donor Fluorophores

A summary of some of the various methods available for synthesizing tandem dyes having violet excitable donor fluorophores can be found in Steward et al., in "Solid Phase Peptide Synthesis", W. H. Freeman Co., San Francisco, 1969; Bodanszky et al., in "Peptide Synthesis", John Wiley & Sons, Second Edition, 1976 and Meienhofer, in "Hormonal Proteins and Peptides", Vol. 2, p. 46, Academic Press (New York), 1983; and Kent, Ann. Rev. Biochem., 57, 957, 1988, for solid phase peptide synthesis, and Schroder et al., in "The Peptides", Vol. 1, Academic Press (New York), 1965 for solution synthesis. Any convenient protecting group strategies may be used such as, but are not limited to, Fmoc solid-phase peptide synthesis and Boc solid-phase peptide synthesis strategies. In Boc solid-phase peptide synthesis a Boc-amino protecting group is used at the amino terminal and benzyl or benzyl-based or other convenient protecting groups may be used for the protection of sidechain functional groups. In Fmoc solid-phase peptide synthesis a Fmoc-amino protecting group is used at the amino terminal and tert-butyl or benzyl-based or other convenient protecting groups may be used for protection of sidechain functional groups. Convenient protecting groups that may be used in such synthetic methods are described in the above references and by McOmic in "Protective Groups in Organic Chemistry", Plenum Press, New York, 1973; and Greene and Wuts, "Protective Groups in Organic Synthesis", John Wiley & Sons, 4th Edition, 2006. Tandem dyes having violet excitable donor fluorophores and different acceptor fluorophores were prepared, i.e., Tandem 570 (having an acceptor that provided for emission at 570 nm), Tandem 600 (having an acceptor that provided for emission at 600 nm), Tandem 650 (having an acceptor that provided for emission at 650 nm), Tandem 712 (having an acceptor that provided for emission at 712 nm), Tandem 750 (having an acceptor that provided for emission at 750 nm), Tandem 780 (having an acceptor that provided for emission at 780 nm), and Tandem 850 (having an acceptor that provided for emission at 850 nm).

IV. Characterization of Sample Tandem Dyes

A. UV-Vis Spectroscopy

A UV-2600 Spectrophotometer (double beam, single monochromator Shimadzu Scientific Instruments) was set to collect data for 1 nm increments at a slit width of 1.0 nm from 900 nm to 250 nm. A stock solution of a Tandem Dye as prepared in III. above, (i.e., Tandem 570, Tandem 600, Tandem 650, Tandem 712, Tandem 750, Tandem 780 or Tandem 850) dissolved in 1× phosphate buffered saline (PBS) was prepared, and 2 mL was transferred to a sample cuvette [1-cm polymethylmethacrylate cuvette]. Then 2 mL of 1×PBS was transferred to a second cuvette. The cuvette containing 1×PBS was placed in the blank cuvette position inside the UV-2600, while the Tandem dye sample sample cuvette was placed in the sample cuvette position. The instrument absorbance was auto-zeroed at 900 nm, and the UV-Vis spectrum was collected from 900 nm to 250 nm.

B. Fluorescence Spectroscopy

Figure 2A:
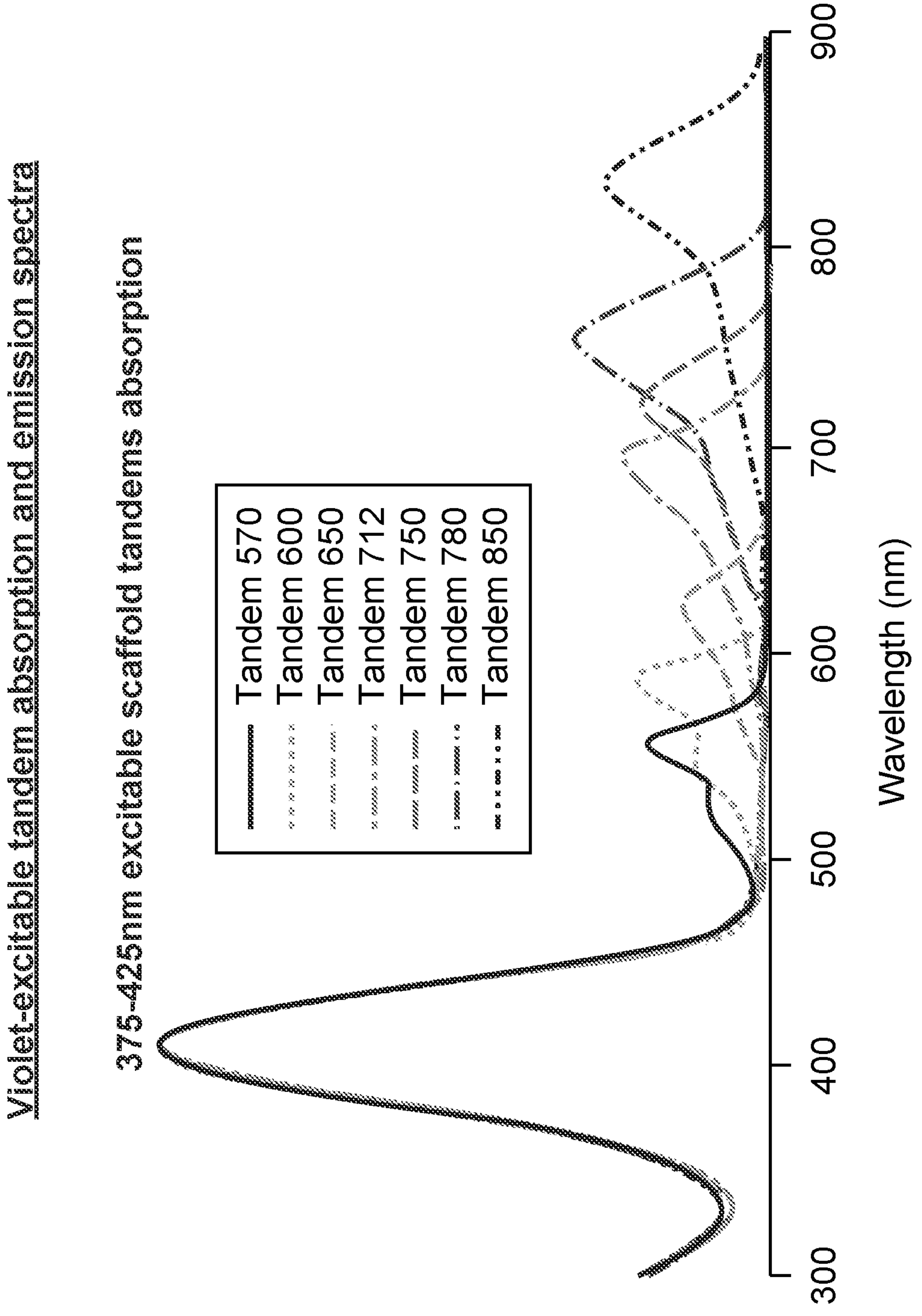
FIG. 2 provides absorption and emission spectra for seven different violet excitable tandem dyes according to embodiments of the invention.
Figure 2B:
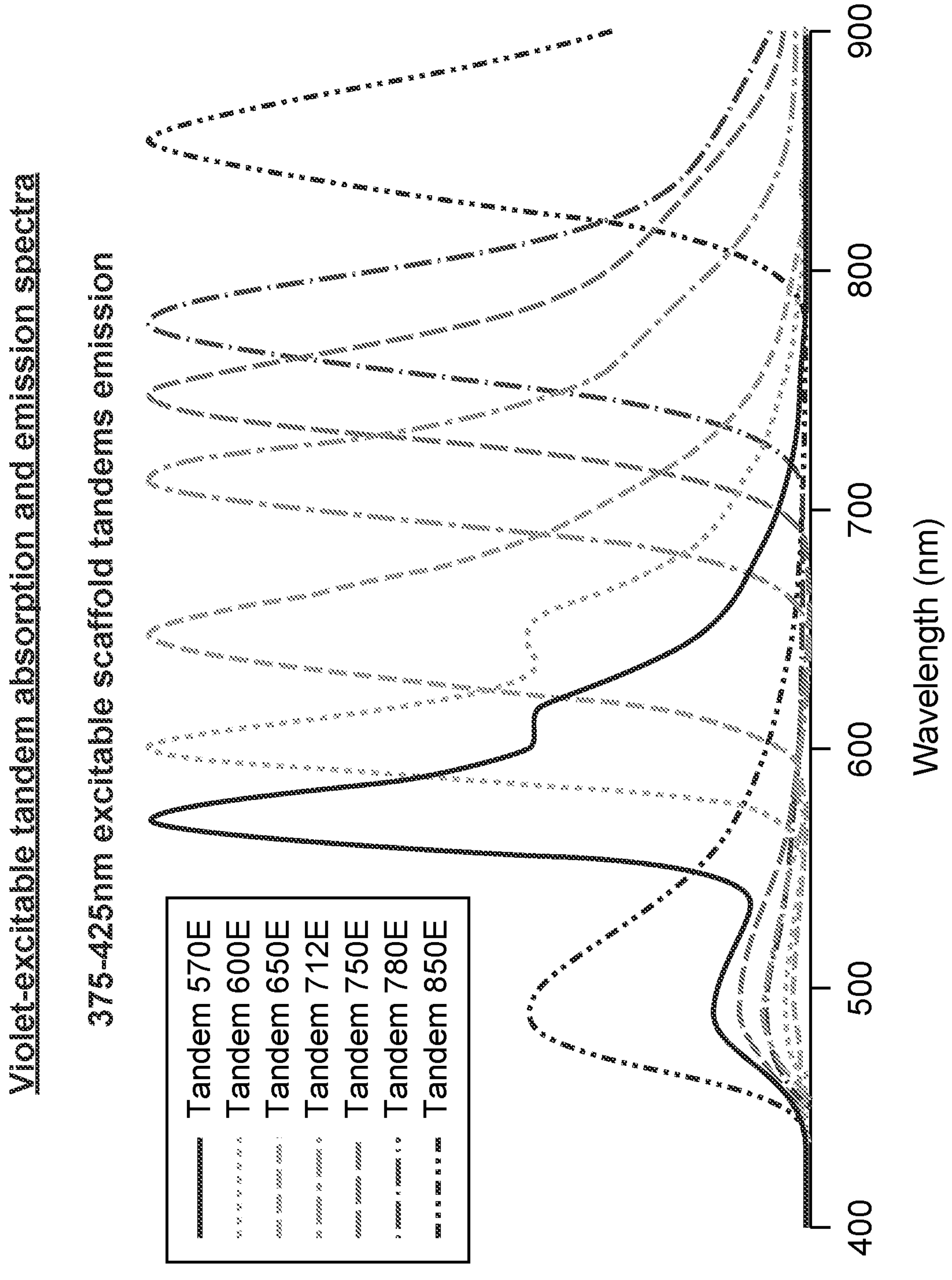

A small volume of a Tandem Dye as prepared in III. above, (i.e., Tandem 570, Tandem 600, Tandem 650, Tandem 712, Tandem 750, Tandem 780 or Tandem 850) stock solution in 1×PBS was diluted to 25 mA.U. in a total volume of 2 mL 1×PBS. This solution was transferred to a sample cuvette [1-cm polymethylmethacrylate cuvette] and placed inside the sample compartment of a fluorometer. The excitation wavelength was set to 405 nm, and the emission scan range was set to 415 nm to 900 nm. For signal detection, fluorescence signal (S1) and instrument noise (R1) were both recorded. A correction file applied to the raw output signals transformed the S1 and R1 signals to corrected fluorescence (S1c) and corrected noise (R1c). The corrected fluorescence S1c was then normalized with respect to the corrected noise to give the final reported fluorescence emission of the sample. The results are provided in FIG. 2.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A tandem dye comprising:

a non-conjugated polymeric backbone;

one or more violet excitable donor fluorophores selected to have an absorption maximum ranging from 375 to 425 nm linked to the non-conjugated polymeric backbone; and one or more acceptor fluorophores linked to the non-conjugated polymeric backbone, wherein the donor and acceptor fluorophores are in energy transfer relationship.

2. The tandem dye according to claim 1, wherein the one or more violet excitable donor fluorophores are selected from the group consisting of coumarin fluorophores, pyrene fluorophores and triphenyl fluorophores.

3. The tandem dye according to claim 2, wherein the one or more violet excitable donor fluorophores are coumarin fluorophores.

4. The tandem dye according to claim 1, wherein the one or more violet excitable donor fluorophores are bonded to a water-solubilizing group.

5. The tandem dye according to claim 4, wherein the water-solubilizing group comprises a non-ionic water solubilizing group.

6. The tandem dye according to claim 5, wherein the non-ionic water-solubilizing group comprises a polyalkylene glycol.

7. The tandem dye according to claim 6, wherein the polyalkylene glycol comprises a polyethylene glycol.

8. The tandem dye according to claim 1, wherein the one or more acceptor fluorophores has an emission maximum ranging from 500 to 875 nm.

9. The tandem dye according to claim 1, wherein the one or more acceptor fluorophores is selected from the group consisting of coumarin dyes, cyanine dyes, rhodamine dyes, xanthene dyes, polymethines, dipyrromethene borondifluorides, napthalimides, thiazine dyes, and acridine dyes.

10. The tandem dye according to claim 1, wherein the number of donor fluorophores exceeds the number of acceptor fluorophores.

11. The tandem dye according to claim 10, wherein the number of donor fluorophores ranges from 2 to 20.

12. The tandem dye according to claim 1, wherein the dye comprise a single acceptor fluorophore.

13. The tandem dye according to claim 1, wherein the tandem dye is linked to a biomolecule.

14. The tandem dye according to claim 13, wherein the biomolecule is selected from the group consisting of carbohydrates, lipids, nucleic acids, and proteins.

15. The tandem dye according to claim 14, wherein the biomolecule is a binding member.

16. The tandem dye according to claim 15, wherein the binding member is an antibody or binding fragment or derivative thereof.

17. The tandem dye according to claim 1, wherein the tandem dye is linked to a chemo-selective group.

18. The tandem dye according to claim 1, wherein the non-conjugated polymeric backbone comprises a peptide.

19. The tandem dye according to claim 18, wherein the peptide comprises from 5 to 100 amino acid residues.

* * * * *